(12) United States Patent
Chen et al.

(10) Patent No.: US 9,708,289 B2
(45) Date of Patent: Jul. 18, 2017

(54) IMIDAZOLE DIKETONE COMPOUND AND USE THEREOF

(71) Applicant: HINOVA PHARMACEUTICALS INC., Chengdu (CN)

(72) Inventors: Yuanwei Chen, ChengDu (CN); Yu Gong, ChengDu (CN)

(73) Assignee: Hinova Pharmaceuticals Inc., Chendu (CN)

( * ) Notice: Subject to any disclaimer, the term of this patent is extended or adjusted under 35 U.S.C. 154(b) by 0 days.

(21) Appl. No.: 14/889,032

(22) PCT Filed: May 27, 2014

(86) PCT No.: PCT/CN2014/078528
§ 371 (c)(1),
(2) Date: Nov. 4, 2015

(87) PCT Pub. No.: WO2014/190895
PCT Pub. Date: Dec. 4, 2014

(65) Prior Publication Data
US 2016/0152592 A1      Jun. 2, 2016

(30) Foreign Application Priority Data

May 29, 2013    (CN) .......................... 2013 1 0205281

(51) Int. Cl.
| | | |
|---|---|---|
| A61K 31/44 | (2006.01) | |
| C07D 211/00 | (2006.01) | |
| C07D 401/04 | (2006.01) | |

(52) U.S. Cl.
CPC .................. C07D 401/04 (2013.01)

(58) Field of Classification Search
CPC .................................................. C07D 401/04
USPC .................. 514/278, 341; 546/15, 274.1
See application file for complete search history.

(56) References Cited

U.S. PATENT DOCUMENTS

| | | |
|---|---|---|
| 8,802,689 B2 | 8/2014 | Jung et al. |
| 9,108,944 B2 | 8/2015 | Smith et al. |

FOREIGN PATENT DOCUMENTS

| | | | |
|---|---|---|---|
| CN | 101454002 A | | 6/2009 |
| CN | 102532099 | * | 7/2012 |
| WO | 2007126765 A2 | | 11/2007 |
| WO | 2008119015 A2 | | 10/2008 |

OTHER PUBLICATIONS

International Search Report, PCT/CN2014/078528, dated Aug. 19, 2014, 2 pages.
Rathkopf et al., "Phase I Study of ARN-509, a Novel Antiandrogen, in the Treatment of Castration-Resistant Prostate Cancer", Journal of Clinical Oncology, Oct. 1, 2013, vol. 31, No. 28, pp. 3525-3530.
Kushner et al., "Pharmacological uses and perspectives of heavy water and deuterated compounds", Can J Physiol Pharmacol. Feb. 1999, 77(2), pp. 79-88.
"ARN-509: A Novel Antiandrogen for Prostate Cancer Treatment", Cancer Res., Mar. 15, 2012, 72(6), pp. 1494-1503.
Burm, A. G. L., et al., "Pharmacokinetics of Lidocaine and Bupivacaine and Stable Isotope Labelled Analogues: A Study in Healthy Volunteers", Biopharmaceutics & Drug Disposition, vol. 9, 85-95 (1988).
Harbeson, Scott L., et al., Chapter 24, "Deuterium in Drug Discovery and Development", Annual Reports in Medicinal Chemistry, vol. 46, 2011, 403-417.
Manley, Paul W., et al., "The kinetic deuterium isotope effect as applied to metabolic deactivation of imatinib to the des-methyl metabolite, CGP74588", Bioorganic & Medicinal Chemistry 21 (2013) 3231-3239.

* cited by examiner

*Primary Examiner* — T. Victor Oh
(74) *Attorney, Agent, or Firm* — Senniger Powers LLP

(57) ABSTRACT

Provided are imidazolidinedione compounds of formula (I), processes for preparation, uses and pharmaceutically compositions thereof. Said imidazolidinedione compounds possess androgen receptor antagonist activity and can be used for preventing and treating diseases and disorders related to androgen receptor, such as prostate cancer, alopecia, hair regeneration, acne and adolescent acne.

7 Claims, No Drawings

IMIDAZOLE DIKETONE COMPOUND AND USE THEREOF

REFERENCE TO RELATED APPLICATIONS

This application is a U.S. national stage application of International Patent Application No. PCT/CN2014/078528, filed May 27, 2015, and claims the benefit of Chinese Application No. 201310205281.X, filed May 29, 2013, the entire disclosures of which are incorporated herein by reference.

TECHNICAL FIELD

The invention relates to the field of medicine, in particular, to imidazolidinedione compounds and uses thereof. More specifically, the invention relates to imidazolidinedione compounds and its use as androgen receptor antagonists or for the treatment and prevention of diseases related to androgen receptor.

BACKGROUND

Prostatic cancer (prostatic carcinoma, abbreviated as PCa) is the most common malignant neoplasm in in male reproductive system. The incidence thereof increases with age, and differs significantly from region to region, which is higher in U.S. and Europe. Second to lung cancer, prostatic cancer is the second cancer leading to death in men. In the past, prostatic cancer has not been paid attention in China, since it belongs to a small disease in the spectrum of tumor. However, with the social development and progress in our country, the aging of society, urbanization, westernization of dietary structure and advances in detection technology, the incidence of prostate cancer was significantly increased. A foreign survey about prostate cancer which was completed by The Second Hospital of Tianjin Medical University and Diagnosis and Treatment of Prostate cancer in Tianjin in 2011 showed that the incidence of prostate cancer in Tianjin was rapidly rising, the incidence of prostate cancer increased by 4 times in 20 years, and the number of patients with prostate cancer accounted for 13.4% of inpatient with urinary tract tumors. Prostatic cancer which was rare cancer in the past becomes common tumors. The incidence of prostate cancer has the same trend in China.

Androgen receptor is a ligand-dependent trans-transcriptional regulatory protein with 110,000 Dalton molecular weight. Androgen receptor plays a very important role in the pathogen and deterioration process of prostate cancer, and in male hormone-related diseases such as acne, male alopecia, and so on.

Traditional methods for treating prostate cancer include surgery or using androgen receptor antagonists such as bicalutamide (Casodex). However, patients will develop drug resistance after 2-4 years treatment, while bicalutamide has side effects of stimulating the proliferation of cancer, therefore patients must stop using bicalutamide. Recent studies have found that bicalutamide will activate androgen receptors, thereby stimulating the proliferation of cancer.

Therefore, there is still a need in the art to develop compounds having superior pharmacodynamic properties to prostatic cancer.

SUMMARY OF INVENTION

The object of the invention is to provide a novel compound having androgen receptor antagonism and the use thereof.

The invention provide an imidazolidinedione compound of formula (I), or a crystal form, pharmaceutically acceptable salt, hydrate or solvate thereof is provided,

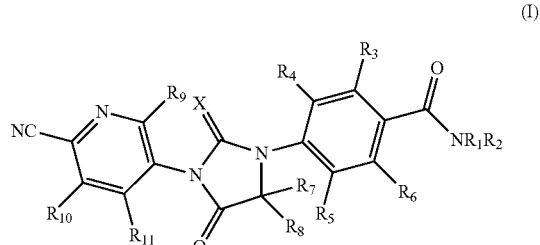

(I)

Wherein, $R_1$ and $R_2$ are independently selected from hydrogen, deuterium, $C_1$-$C_4$ alkyl and one or more deuterium-substituted or perdeuterated $C_1$-$C_4$ alkyl, $R_1$ and $R_2$ are not simultaneously hydrogen;

$R_3$ is hydrogen, deuterium or halogen;

$R_4$, $R_5$, $R_8$, $R_9$, $R_{11}$ are hydrogen, deuterium or halogen (such as F, Cl, Br, or I);

$R_7$ and $R_8$ are independently selected from $C_1$-$C_4$ alkyl and one or more deuterium-substituted or perdeuterated $C_1$-$C_4$ alkyl, or $R_7$ and $R_8$ are joined to form $C_3$-$C_5$ cycloalkyl or one or more deuterium-substituted or perdeuterated $C_3$-$C_5$ cycloalkyl;

$R_{10}$ is non-deuterated, one or more deuterium-substituted or perdeuterated $C_1$-$C_4$ alkyl, or one or more halogen-substituted or perhalogen-substituted $C_1$-$C_4$ alkyl; X is S or O;

Among that, at least one of $R_1$ and $R_2$ is $C_1$-$C_4$ alkyl or one or more deuterium-substituted or perdeuterated $C_1$-$C_4$ alkyl.

In one embodiment, when $R_1$ is hydrogen, at least one of $R_2$, $R_3$, $R_4$, $R_5$, $R_6$, $R_7$, $R_8$, $R_9$, $R_{10}$, $R_{11}$ is deuterium or one or more deuterium-substituted or perdeuterated alkyl.

In one embodiment, (1) when $R_1$ and $R_2$ are methyl, at least one of $R_3$, $R_4$, $R_5$, $R_6$, $R_7$, $R_8$, $R_9$, $R_{10}$, $R_{11}$ is deuterium or one or more deuterium-substituted or perdeuterated alkyl; (2) or when $R_1$ and $R_2$ are methyl, at least one of $R_3$, $R_4$, $R_5$, $R_6$, $R_7$, $R_8$, $R_9$, $R_{10}$, $R_{11}$ is hydrogen or non-deuterated alkyl; (3) $R_7$ and $R_8$ are joined to form $C_4$-$C_6$ cycloalkyl or one or more deuterium-substituted or perdeuterated $C_4$-$C_6$ cycloalkyl.

In one embodiment, $R_1$ is hydrogen, $R_6$ is halogen, $R_7$ and $R_8$ are joined to form $C_4$-$C_6$ cycloalkyl or one or more deuterium-substituted or perdeuterated $C_4$-$C_6$ cycloalkyl, $R_{10}$ is selected from perhalogenated $C_1$-$C_4$ alkyl.

In one embodiment, the halogen is F.

In one embodiment, $C_1$-$C_4$ alkyl is selected from methyl or ethyl.

In one embodiment, $C_1$-$C_4$ alkyl is selected from methyl, one or more deuterium-substituted or perdeuterated $C_1$-$C_4$ alkyl is selected from mono-deuterated methyl, bi-deuterated methyl, tri-deuterated methyl.

In one embodiment, the compound is selected from the group consisting of

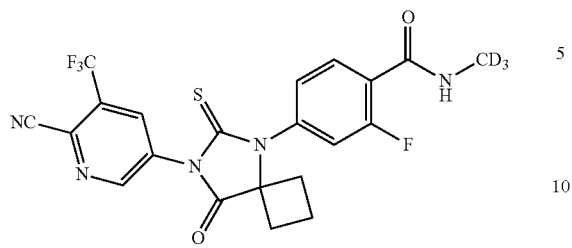
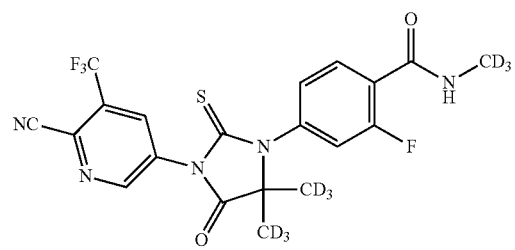
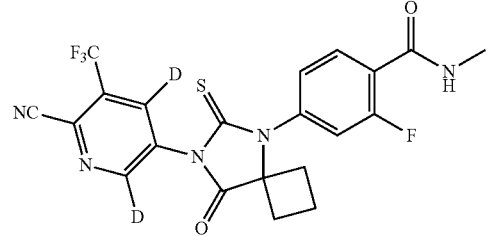
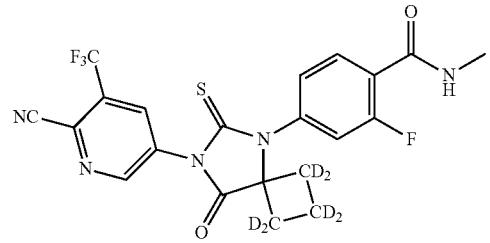
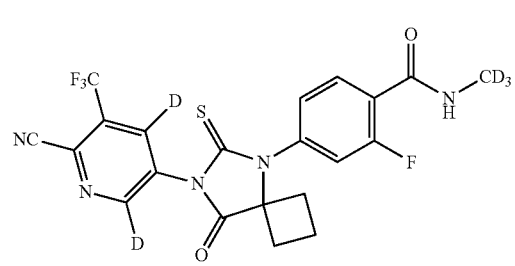
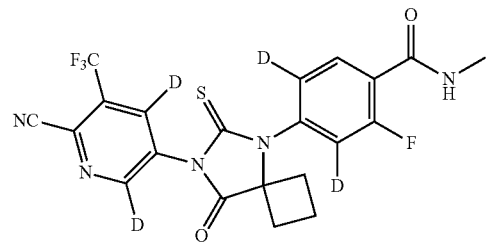
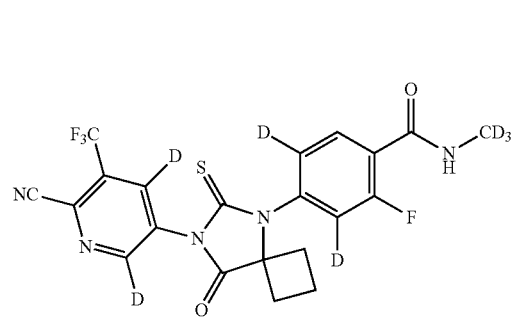

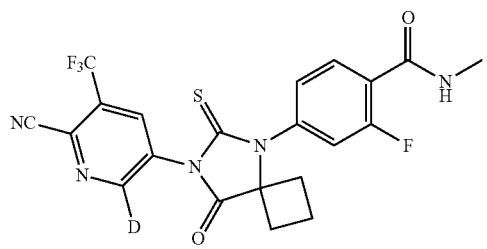

40

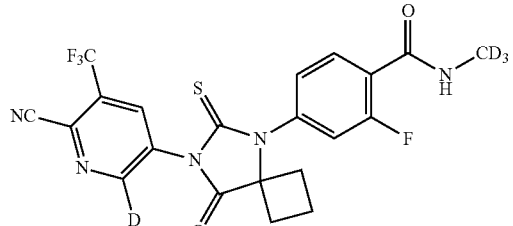

41

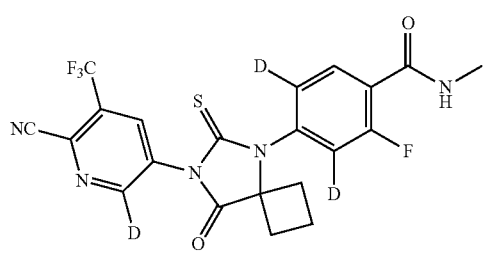

42

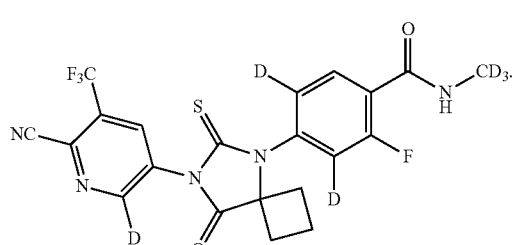

43

In one embodiment, the compound is selected from the group consisting of

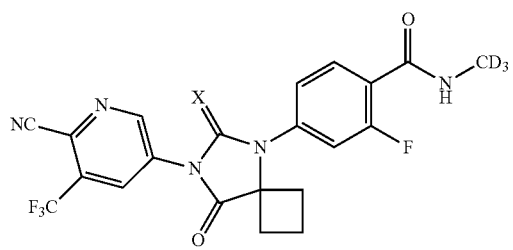

14

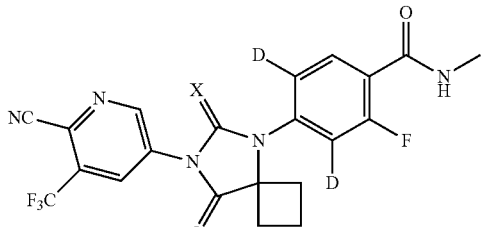

17

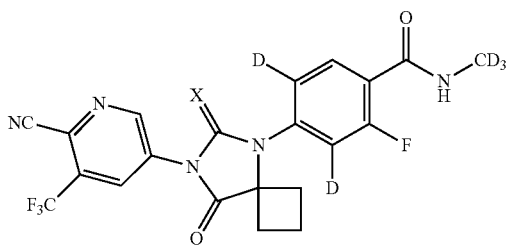

20

In one embodiment, the compound is selected from the group consisting of

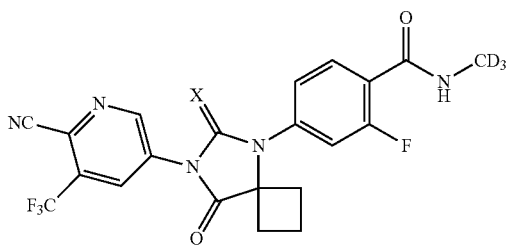

14

In the second aspect of the invention, a method for preparing a pharmaceutical composition is provided, comprising mixing the compound of the first aspect of the invention, or a crystal form, pharmaceutically acceptable salt, hydrate or solvate thereof and a pharmaceutically acceptable carrier to form a pharmaceutical composition.

In the third aspect of the invention, a pharmaceutical composition is provided, comprising (1) the compound of the first aspect of the invention, or a crystal form, pharmaceutically acceptable salt, hydrate or solvate thereof, and (2) a pharmaceutically acceptable carrier.

In one embodiment, the pharmaceutical composition further comprises an additional therapeutic agent; preferably, the additional therapeutic agent is the therapeutic agent for treating alopecia, hair regeneration, pimples, acne or prostate cancer.

In the fourth aspect of the invention, provided is a use of the compound of the first aspect of the invention or a crystal form, pharmaceutically acceptable salt, hydrate or solvate thereof as an androgen receptor antagonist or for preparing drugs for treating and preventing diseases related to androgen receptor activity.

In one embodiment, the disease is selected from the group consisting of alopecia, hair regeneration, pimples, acne and prostate cancer.

In one embodiment, the composition is injection, capsules, tablets, pills, powder or granules.

In the fifth aspect of the invention, a treatment method is provided, comprising a step of administering the compound of the first aspect of the invention, or a crystal form, pharmaceutically acceptable salt, hydrate or solvate thereof or the pharmaceutical composition of the third aspect of the invention to a object in need thereof.

In one embodiment, the object is a person suffering from androgen receptor activity related disease.

In the sixth aspect of the invention, a method for preparing the compound of formula (I) of the first aspect of the invention is provided, comprising steps of:

in a acidic solvent, in the presence of cyanide, reacting compound 5a with $R_7C(O)R_8$, to form compound 6a,

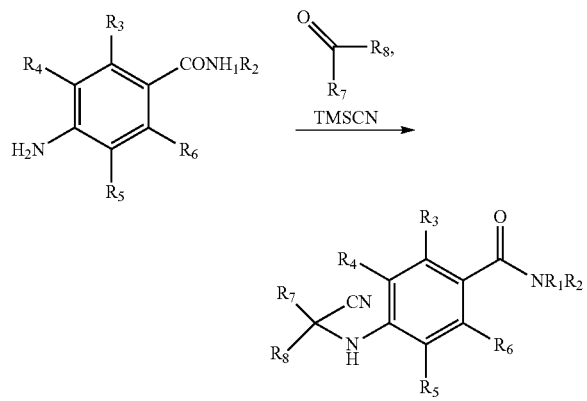

wherein, the cyanide is TMSCN, sodium cyanide or potassium cyanide, (2) in an aprotic solvent, under an acidic condition, reacting compound 2a with compound 6a, to form the compound of formula (I),

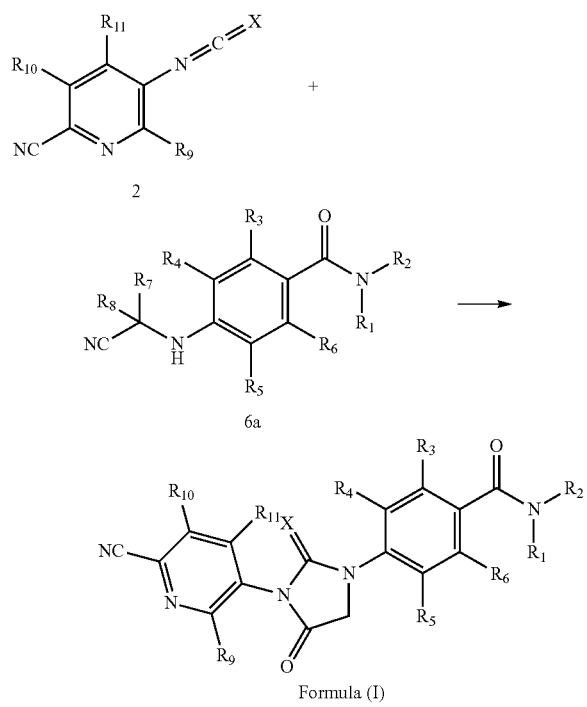

wherein, $R_1$, $R_2$, $R_3$, $R_4$, $R_5$, $R_6$, $R_7$, $R_8$, $R_9$, $R_{10}$, $R_{11}$, or X is defined as those in the first aspect of the invention.

In one embodiment, in step (2), the reaction is conducted in the presence of hydrochloric acid or sulfuric acid.

Further, the compound 5a may be prepared by the following steps:

(1) in an inert solvent, reacting compound 3a with $NHR_1R_2$, to form compound 4a;

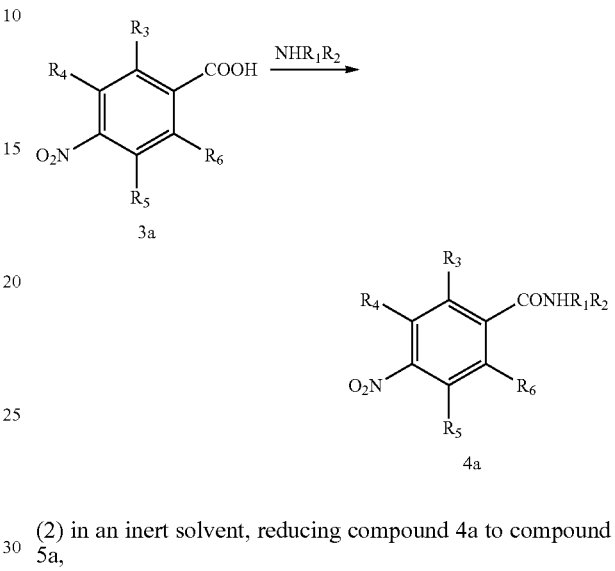

(2) in an inert solvent, reducing compound 4a to compound 5a,

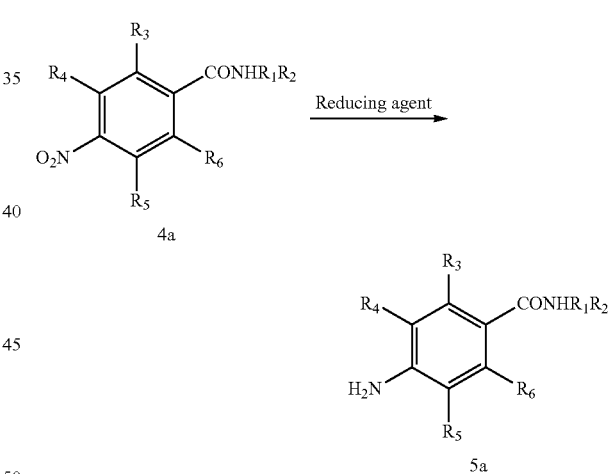

Wherein, $R_1$, $R_2$, $R_3$, $R_4$, $R_5$, $R_6$ are defined as those in the first aspect of the invention.

In one embodiment, reduction is conducted with a reducing reagent selected from the group consisting of iron powder, zinc powder, and the combination thereof.

In one embodiment, the acidic solvent in step (1) is methanoic acid, acetic acid, an aqueous solution of hydrochloric acid with a mass concentration of 1-5% or an aqueous solution of sulfuric acid with a mass concentration of 1-5%.

In one embodiment, the aprotic solvent in step (2) is dimethyl formamide (DMF), dimethyl sulfoxide (DMSO), or $CH_3CN$.

In one embodiment, the inert solvent is methylene chloride, ethyl acetate, tetrahydrofuran, chloroform, or acetonitrile.

It should be understood that in the present invention, the technical features specifically described above and below (such as the Examples) can be combined with each other, thereby constituting a new or preferred technical solution, which needs not be specified.

DETAILED DESCRIPTION OF INVENTION

Through intensive research, the inventors unexpectedly discovers that, the imidazolidinedione compounds of formula (I) of the present invention, or a crystal form, pharmaceutically acceptable salt, hydrate or solvate thereof have excellent pharmacokinetics and/or pharmacodynamic properties, therefore are more suitably used as androgen receptor antagonists, and are more suitably used for the preparation of drugs for treating androgen-related diseases (such as cancer). Based on this discovery, the inventors complete the present invention.

Definition

As used herein, the term "halogen" refers to F, Cl, Br and I. Preferably, halogen is selected from F, Cl, and Br.

As used herein, the term "alkyl" refers to a straight chain or branched-chain alkyl. Preferably, alkyl is $C_1$-$C_4$ alkyl, such as methyl, ethyl, propyl, iso-propyl, butyl, iso-butyl, tert-butyl and the like.

As used herein, the term "deuterated" means that hydrogen(s) in a compound or group is substituted by deuterium(s). "Deuterated" can be mono-substituted, bi-substituted, multi-substituted or total-substituted. The terms "one or more deuterium-substituted" and "substituted by deuterium for once or more times" can be used interchangeably.

In one embodiment, the deuterium content in a deuterium-substituted position is greater than the natural abundance of deuterium (0.015%), preferably >50%, more preferably >75%, more preferably >95%, more preferably >97%, more preferably >99%, more preferably >99.5%.

Active Ingredients

As used herein, the term "compound of the invention" refers to the compound of formula (I). This term also includes various crystal forms, pharmaceutically acceptable salts, hydrates or solvates of the compound of formula (I).

As used herein, the term "pharmaceutically acceptable salt" refers to the salts which are suitable for medicine and formed by the compound of the invention with an acid or a base. Pharmaceutically acceptable salts include inorganic salts and organic salts. A preferred salt is formed by the compound of the invention with an acid. The acid suitable for forming salts includes, but not limited to, inorganic acid, such as hydrochloric acid, hydrobromic acid, hydrofluoric acid, sulfuric acid, nitric acid, phosphoric acid; organic acid, such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzene methanesulfonic acid, benzene sulfonic acid; and acidic amino acid, such as aspartic acid, glutamic acid.

Pharmaceutical Composition and the Administration Thereof

The compounds of the invention possess outstanding androgen receptor antagonism, therefore, the compounds of the invention and the crystal forms, the pharmaceutically acceptable inorganic or organic salts, hydrates or solvates thereof, and the pharmaceutical compositions comprising compounds of the invention as the main activity ingredient, can be used for treating, preventing and alleviating diseases mediated by androgen. According to the prior art, the compounds of the invention can be used to treat the following diseases: alopecia, hair regeneration, pimples, acne, or prostate cancer etc.

Pharmaceutical composition of the invention comprises a safe and effective amount of the compounds of the invention or the pharmaceutical acceptable salts thereof and pharmaceutically acceptable excipients or carriers. Wherein "safe and effective amount" refers to an amount of the compounds which is sufficient to improve the patient's condition and would not induce serious side effect. Generally, the pharmaceutical composition contains 1-2000 mg compounds of the invention/dose, preferably, 10-200 mg compounds of the invention/dose. Preferably, "one dose" refers to a capsule or tablet.

"Pharmaceutically acceptable carrier" means: one or more compatible solid or liquid fillers or gel material, which are suitable for human, and must have sufficient purity and sufficiently low toxicity. "Compatibility" herein means that the components of the compositions can be blended with the compounds of the invention or with each other, and would not significantly reduce the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

The application manner for the compounds or pharmaceutical compositions of the invention is not specially limited, and the representative application manner includes (but not limited to): oral, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or di-calcium phosphate, or mixed with the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and gum arabic; (c) humectant, such as, glycerol; (d) disintegrating agents such as agar, calcium carbonate, potato starch or tapioca starch, alginic acid, certain complex silicates, and sodium carbonate; (e) dissolution-retarding agents, such as paraffin; (f) absorption accelerators, for example, quaternary ammonium compounds; (g) wetting agents, such as cetyl alcohol and single glyceryl stearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffer.

The solid dosage forms such as tablets, sugar pills, capsules, pills and granules can be prepared by using coating and shell material, such as enteric coatings and other materials known in the art. They can contain opaque agent, and the release of the active compounds or compounds in such compositions can be delayed for releasing in certain portion of the digestive tract. Instance of the embedding components can be polymers and waxes. If necessary, the active compounds and one or more above excipients can be prepared into microcapsules.

Liquid dosage forms for oral administration include pharmaceutically acceptable emulsions, solutions, suspensions, syrups or tinctures. In addition to the active compounds, the liquid dosage forms may contain conventional inert diluent known in the art, such as water or other solvent, solubilizer and emulsifier, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixtures thereof and so on.

Besides the inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the mixtures thereof and so on.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and the suitable mixtures thereof.

The dosage forms of compounds of the invention for topical administration include ointments, powders, patches, aerosol, and inhalants. The active ingredients are mixed with physiologically acceptable carriers and any preservatives, buffers, or propellant if necessary, under sterile conditions.

The compounds of the invention can be administered alone, or in corn bination with other pharmaceutically acceptable compounds.

When the pharmaceutical compositions are used, a safe and effective amount of compounds of the present invention is applied to mammals in need thereof (such as human), wherein the applied amount is the pharmaceutically effective amount. For a person weighted 60 kg, the daily dose is usually 1~2000 mg, preferably 20~500 mg. Of course, the particular dose should also depend on other factors, such as the route of administration, patient healthy status etc., which are well within the skill of a skilled physician.

Preparation

The preparation methods of compound (I) of the present invention are described in detail as below. However, these specific methods are not provided for the limitation of the invention. The compounds of the invention can be readily prepared by optionally combining any of the various methods described in the specification or various methods known in the art, and such combination can readily be carried out by the skilled in the art.

The compound of formula (I) of the present invention can be prepared according to the following synthetic scheme. In general, during the preparation, each reaction is conducted in solvent, at a temperature between room temperature to reflux temperature (such as 0-120° C., preferably 0-80° C.). Generally, the reaction time is 0.1-60 hours, preferably, 0.5-48 hours.

Preferably, the preparation method for compound (I) is as follows:

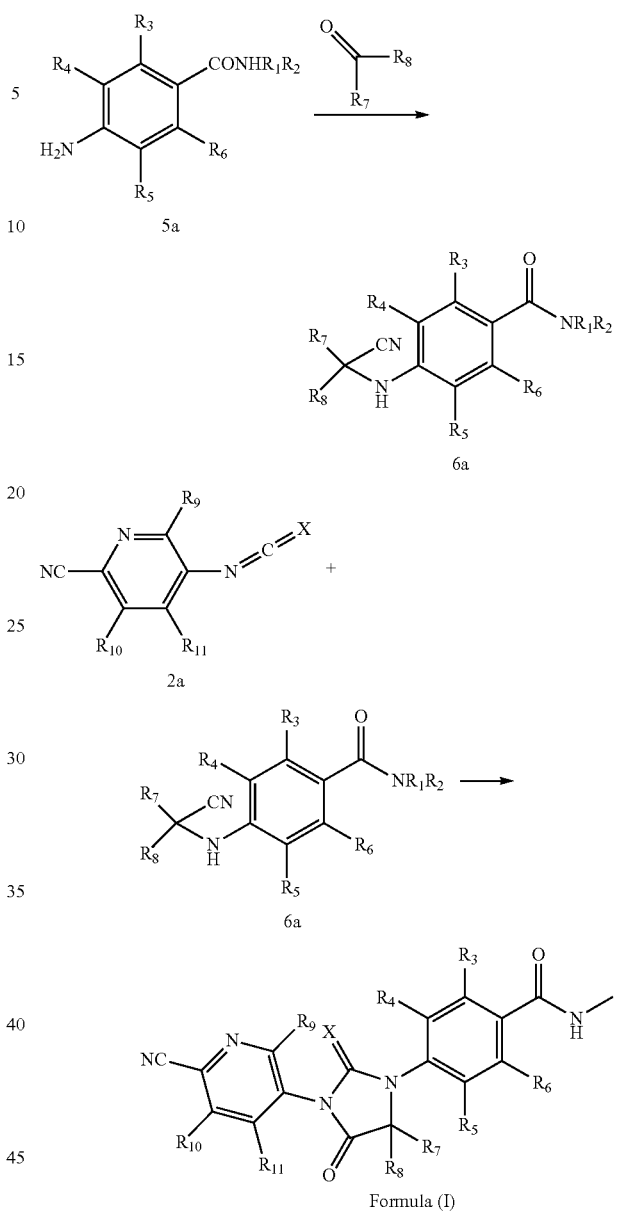

wherein $R_1$, $R_2$, $R_3$, $R_4$, $R_5$, $R_6$, $R_7$, $R_8$, $R_9$, $R_{10}$, $R_{11}$, and X are defined as those in formula (I).

The corresponding deuterated compounds can be prepared by using the corresponding starting deuterated compound or corresponding deuterated reagents as the starting material, such as deuterated methylamine, deuterated acetone and through the same route. The starting material with deuteration on benzene ring can be prepared by the following methods or literature (Org Letter, 2008, 4351-4353).

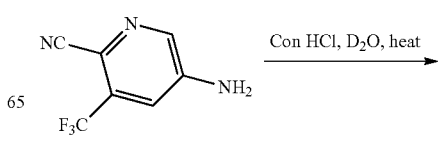

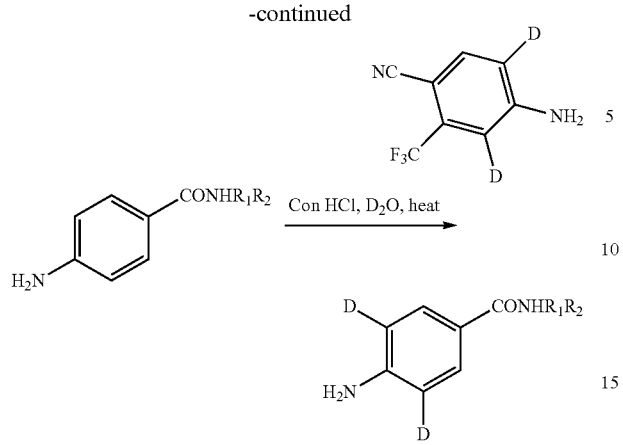

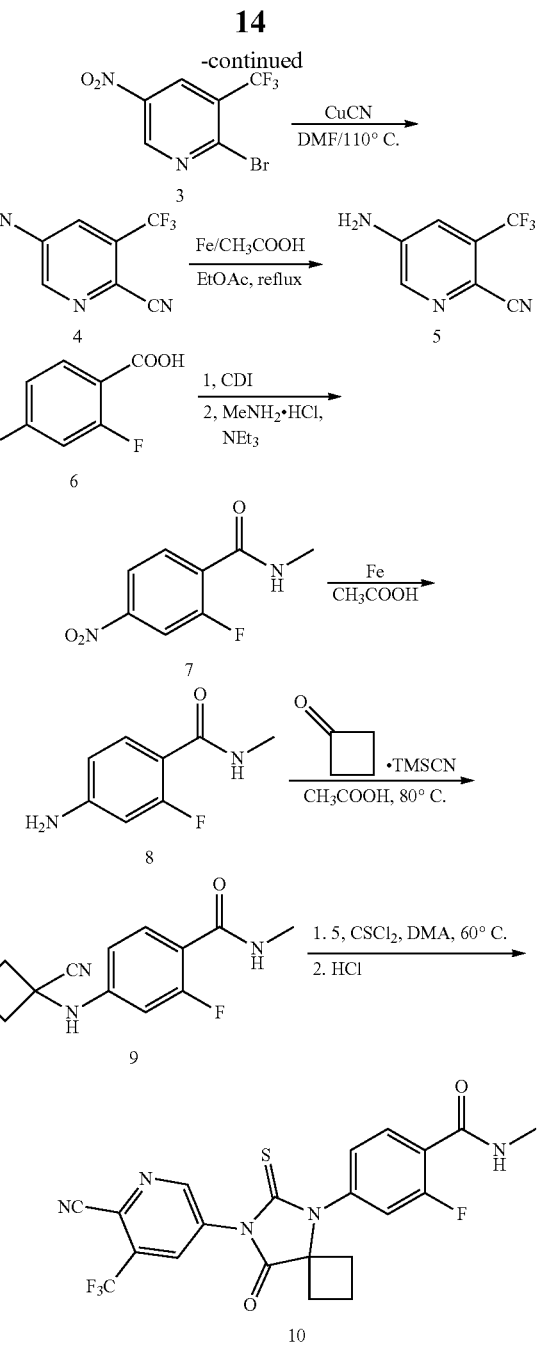

The present invention will be further illustrated below with reference to the specific examples. It should be understood that these examples are only to illustrate the invention but not to limit the scope of the invention. Unless indicated otherwise, parts and percentage are calculated by weight.

The "reflux" refers to reflux, the "M.W." refers to microwave, "Con HCl" represents concentrated hydrochloric acid.

In the present patent, the utilization of deuterated form was to modify the original compound structure. Summary of deuterated drug studies was published in 1975 (Studies with deuterated drugs, Journal of Pharmaceutical Sciences, 1975, 64(3):367-391) which noted that the change of half-life or activity of the drug after deuterated have unpredictable. However, the experiment of the present invention had found that the pharmacokinetic properties and pharmacodynamic activities of the resulting deuterated compound were obviously better than the original compound, as well as unexpected technical effect. They are more suitable used as androgen receptor antagonists and prepared to treat androgen-related diseases such as hair loss, hair regeneration, prostate cancer, pimples, etc.

It should be understood, within the scope of the present invention, each of the above technical features of the present invention and the technical features below (e.g. Examples) specifically described can be combined with each other to form a new or preferred technical solution. Due to paragraph limitation, this is no longer tautology.

DETAILED DESCRIPTION

Example 1

Synthesis of 4-[7-(6-cyano-5-trifluoromethyl-3-pyridyl)-8-oxo-6-thio-5, 7-diazaspiro [3, 4]-5-octyl]-2-fluoro-N-methyl-benzamide (compound 10)

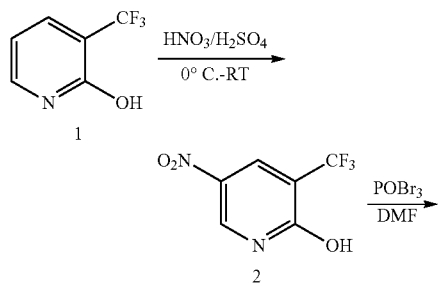

Synthesis of 5-nitro-3-trifluoromethyl-2-hydroxypyridine (Intermediate 2)

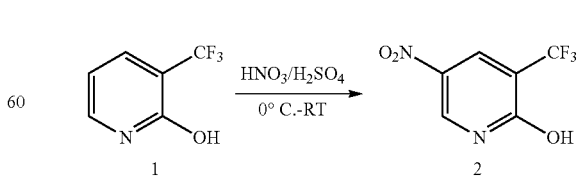

In an ice bath, 2-hydroxy-3-trifluoromethylpyridine (25 g, 0.15 mol) was added into cold concentrated sulfuric acid (150 ml), followed by drop wise addition of concentrated nitric acid (58 ml). The reaction mixture was warmed to room temperature and was stirred at room temperature for 4 h, and the reaction mixture was poured into 1 liter of icy water to afford white solids. The solids were filtered off and washed with water twice and dried to afford the first batch of compound 2 (16.97 g). The filtrate was adjusted to weak acidic by 10M sodium hydroxide, and the solution was extracted by 200 ml ethyl acetate for three times. The combined organic phases were dried over anhydrous sodium sulfate, and the solvent was removed. The residue was purified by column chromatography (mobile phase, DCM/MeOH) to give the second batch of compound 2 (6.81 g). Total yield was 74.5%.

Synthesis of 5-nitro-trifluoromethyl-2-bromo-3-pyridine (Intermediate 3)

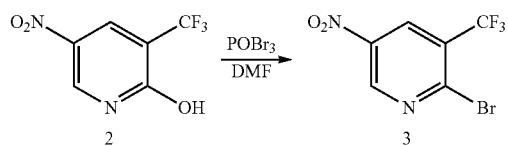

To the mixture of compound 2 (2.5 g, 12 mmol) and POBr$_3$ (10 g, 34.8 mmol) DMF (0.5 ml) was added in, and the reaction was heated to 110° C. for 4 h. The reaction mixture was poured into 100 g ice, and pH was adjusted to neutral, followed by extraction with ethyl acetate for three times. The combined organic phases were dried over anhydrous sodium sulfate, and the solvent was removed. The residue was purified by column chromatography (mobile phase, PE) to give compound 3 (3.2 g, 98% yield). $^1$H NMR (CDCl$_3$, 400 MHz): δ 9.09 (1H, d, J=2.8 Hz), 8.60 (1H, d, J=2.8 Hz) ppm.

Synthesis of 5-nitro-3-trifluoromethyl-2-cyanopyridine (Intermediate 4)

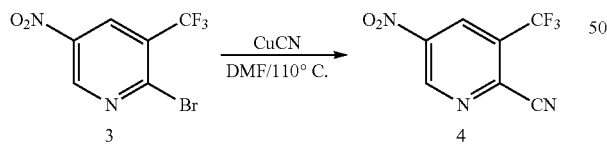

Compound 3 (2.55 g, 9.4 mmol) was dissolved in DMF (10 ml) and heated to 100° C., followed by the addition of CuCN (1.01 g, 11.2 mmol). The mixture was stirred at 110° C. for 4 h. 100 ml cold water was added to quench the reaction, and then the mixture was extracted with ethyl acetate for three times. The combined organic phases were dried over anhydrous sodium sulfate, and the solvent was removed. The residue was purified by column chromatography to give compound 4 (1.15 g, 52.5% yield).

Synthesis of 5-amino-3-trifluoromethyl-2-cyanopyridine (Intermediate 5)

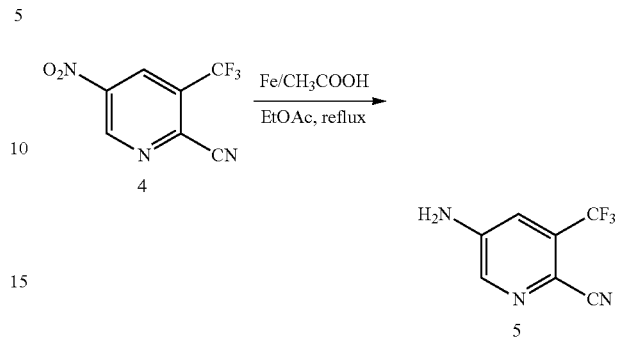

To a mixture of compound 4 (1.15 g, 4.9 mmol) in EtOAc (20 mL) and CH$_3$CO$_2$H (4 mL), iron powder (890 mg) was added. The mixture was refluxed for 16 h before cooling to room temperature. Then solids were filtered off, followed by washed with ethyl acetate for three times, and the combined organic phases were dried over anhydrous sodium sulfate, the solvent was removed to afford the residue, which was purified by column chromatography to give compound 5 as light brown solid (540 mg, 54.5% yield). $^1$H NMR (CDCl$_3$, 400 MHz): δ 8.23 (1H, d, J=2.8 Hz), 7.20 (1H, d, J=2.8 Hz), 4.51 (2H, br) ppm.

Synthesis of 2-fluoro-N-methyl-4-cyano-benzamide (Intermediate 7)

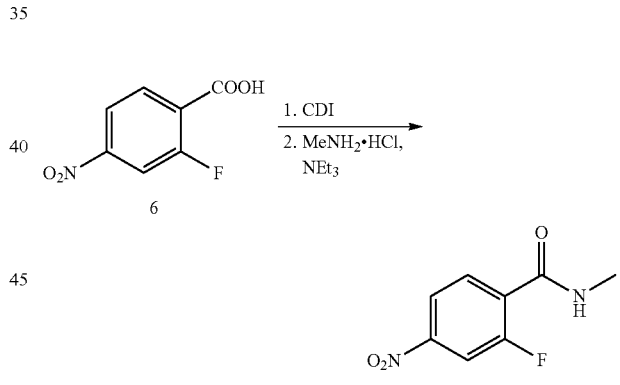

2-fluoro-N-methyl-4-cyano-benzoic acid (6) (25 g, 135.06 mml) was dissolved in DCM (200 ml), followed by addition of CDI (32.8 g, 202.28 mmol). The mixture was stirred for 1 h at room temperature. Triethylamine (20.47 g, 202.29 mmol) was added into the solution of methylamine hydrochloride (10.94 g, 162.12 mmol) in DCM (50 ml), and stirred for 0.5 h at room temperature to afford the suspension solution, which was transferred into the reaction mixture for stirring up to 1 h. The reaction was quenched by addition of H$_2$O (100 ml), followed by extraction by DCM twice, and the combined organic phases were washed by 1M HCl, 1M NaOH twice and brine once, dried over anhydrous sodium sulfate, the solvent was removed to afford the residue, which was purified by column chromatography to give compound 5 as white solid (14.61 g, 55% yield). M.S.: 199.2 (M+H$^+$).

Synthesis of 2-fluoro-N-methyl-4-amino-benzamide (Intermediate 8)

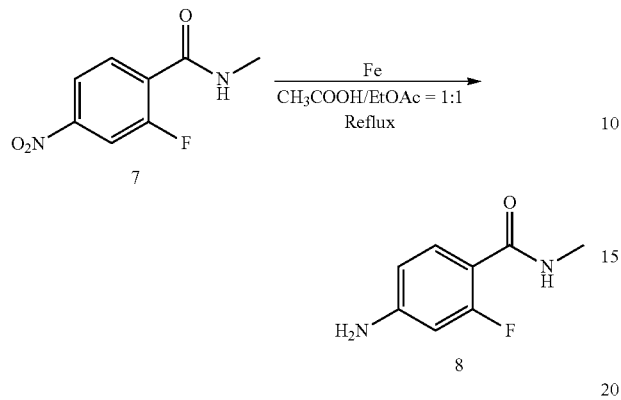

Compound 7 (14.6 g, 73.7 mmol) was dissolved in a solution of ethyl acetate and acetic acid (50 ml:50 ml). Iron powder (39 g) was added. The resulting mixture was refluxed overnight for 16 h, and then cooled to room temperature. The solid was filtered and washed three times with ethyl acetate (3×50 ml). The combined organic phases were washed with brine, dried over sodium sulfate and concentrated the residue was purified by column chromatography (DCM:MeOH=50:1) to give a pale yellow solid of compound 8 (7.62 g, 61.5% yield). $^1$H NMR (CDCl$_3$, 400 MHz): δ 7.92 (1H, m), 6.60 (1H, s), 6.49 (1H, d, J=8.4 Hz), 6.32 (1H, d, J=14 Hz), 4.10 (2H, s), 2.99 (3H, s) ppm.

Synthesis of 4-(1-cyano-cyclobutanylamino)-2-fluoro-N-methyl-benzamide (Intermediate 9)

TMSCN (1.77 g, 17.54 mmol), cyclobutanone (0.89 mL, 11.88 mmol) and compound 8 (1.00 g, 5.95 mmol) were dissolved in acetic acid (10 mL). The resulting mixture was reacted at 80° C. for 16 h. Water (10 mL) was added in and it was extracted with ethyl acetate twice. The organic phases were washed with brine, dried over sodium sulfate and concentrated. The residue was washed with petroleum ether (10 mL) to give compound 13 as a brown solid (1.32 g, 90% yield). $^1$H NMR (DMSO-d$_6$, 400 MHz): δ 7.99 (1H, m), 6.70 (1H, s), 6.49 (1H, d, J=8.8 Hz), 6.30 (1H, d, J=14.4 Hz), 4.62 (1H, s), 3.01 (3H, d, J=4.8 Hz), 2.84 (2H, m), 2.40 (2H, m), 2.27 (1H, m), 2.20 (1H, m) ppm.

Synthesis of 4-[7-(6-cyano-5-trifluoromethyl-3-pyridyl)-8-oxo-6-thio-5, 7-diazaspiro [3, 4]-5-octyl]-2-fluoro-N-methyl-benzamide (compound 10)

To the mixture of compound 9 (68 mg, 0.26 mmol) and compound 5 (50 mg, 0.26 mmol) in DMA (10 ml), thiophosgene (32 mg, 0.26 mmol) was added in dropwise. The mixture was heated to 60° C. for 16 h, and then methanol (10 mL), water (10 mL) and concentrated hydrochloric acid (2 mL) were added in and the mixture was heated at reflux for 1 h. The resulting mixture was extracted with ethyl acetate, washed with brine, dried over sodium sulfate, concentrated and purified by column chromatography (PE:EA/1:1) to give a brown solid as crude product, which was purified by preparative chromatography to give compound 10 as a white solid (51.3 mg, 40.4% yield). $^1$H NMR (CD$_3$OD, 400 MHz): δ 9.17 (1H, d, J=2.0 Hz), 8.65 (1H, d, J=2.0 Hz), 7.95 (1H, m), 7.41 (2H, m), 2.98 (3H, s), 2.73 (2H, m), 2.60 (2H, m), 2.16 (1H, m), 1.67 (1H, m) ppm. MS: 481.2 (M+H$^+$).

Example 2

Synthesis of 4-[7-(6-cyano-5-trifluoromethyl-3-pyridyl)-8-oxo-6-thio-5, 7-diazaspiro [3, 4]-5-octyl]-2-fluoro-N-trideuterated methyl-benzamide (compound 14)

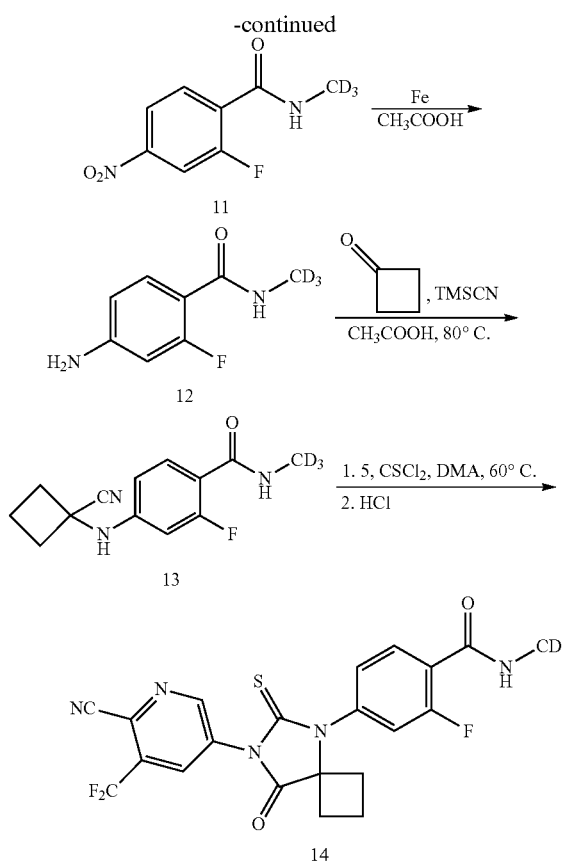

Synthesis of
2-fluoro-N-trifluoromethyl-4-nitro-benzamide
(Intermediate 11)

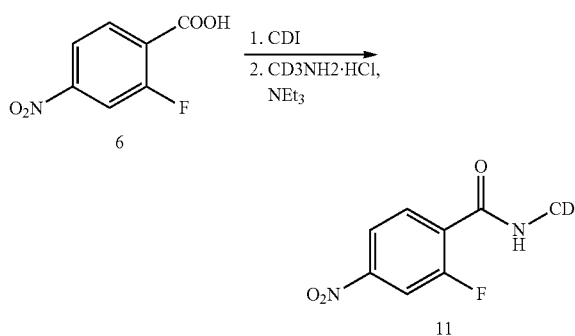

To a dichloromethane solution (20 mL) of compound 6 (5.25 g, 28.37 mmol), CDI (4.62 g, 28.37 mmol) was added in. The reaction mixture was stirred at room temperature for one hour followed by the addition of a dichloromethane solution (20 mL) of trideuterated methylamine hydrochloride (2 g, 28.76 mmol) and triethylamine (3.27 g, 32.36 mmol). The mixture was then stirred at room temperature for an hour. The reaction was quenched by water (10 mL). The organic phase was separated, and the aqueous phase was extracted twice with dichloromethane (2×20 mL). The organic phases were combined, washed with 1 M hydrochloric acid twice (2×10 mL), 1 M aqueous sodium hydroxide solution twice (2×10 mL) and saturated brine (10 mL), The organic phase was dried ($Na_2SO_4$), filtered and concentrated under reduced pressure to give a white solid 11 (Intermediate 11, 5.1 g, 88.2% yield). MS: 202.1 ($M+H^+$).

Synthesis of
2-fluoro-N-trideuteromethyl-4-amino-benzamide
(Intermediate 12)

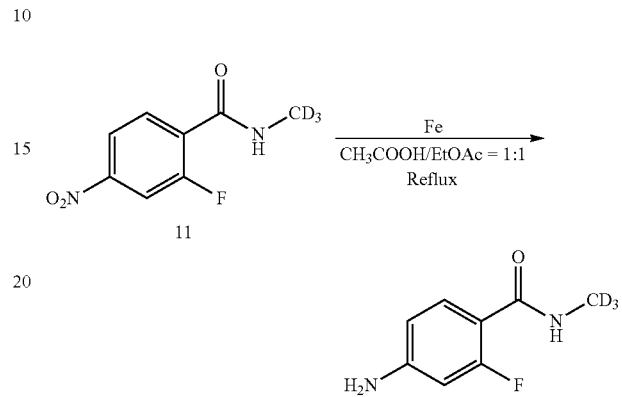

Compound 11 (5.1 g, 25.37 mmol) was dissolved in a solution of ethyl acetate and acetic acid (15 ml+15 ml). 15 g of iron powder was added in. The resulting mixture was refluxed overnight (16 h), and then cooled to room temperature. The solid was filtered and washed three times with ethyl acetate (3×20 ml). The combined organic phases were washed with brine, dried over sodium sulfate and concentrated the residue was purified by column chromatography (DCM:MeOH=50:1) to give a pale yellow solid of compound 12 (2.22 g, 51.2% yield). $^1H$ NMR ($CDCl_3$, 400 MHz): δ 7.92 (1H, m), 6.59 (1H, s), 6.49 (1H, d, J=8.4 Hz), 6.32 (1H, d, J=14.4 Hz), 4.10 (2H, s) ppm.

Synthesis of 4-(1-cyano-cyclobutylamino)-2-fluoro-N-trifluoromethyl-benzamide (Intermediate 13)

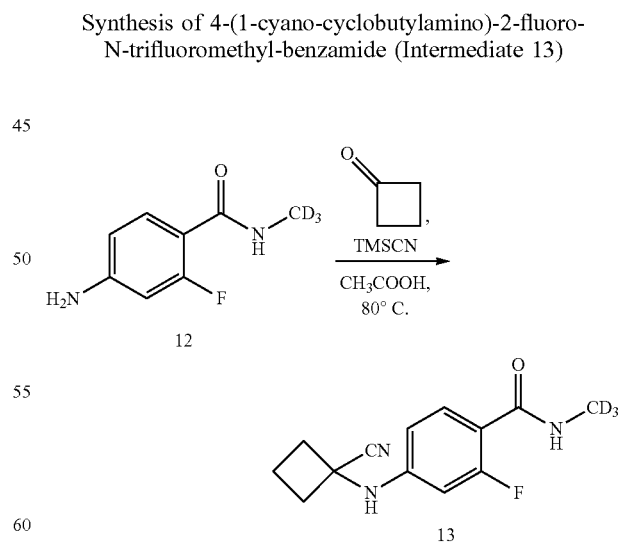

TMSCN (1.77 g, 17.54 mmol), cyclobutanone (0.89 mL, 11.88 mmol) and compound 12 (1 g, 5.95 mmol) were dissolved in acetic acid (10 mL). The resulting mixture was reacted at 80° C. for 16 h. Water (10 mL) was added in and it was extracted with ethyl acetate. The organic phase was washed with brine, dried over sodium sulfate and concentrated. The residue was washed with petroleum ether (10 mL) to give compound 13 as a brown solid (1.31 g, 90% yield). $^1$H NMR (DMSO-$d_6$, 400 MHz): δ 7.79 (1H, s), 7.56 (1H, m), 7.36 (1H, s), 6.46 (1H, d, J=8.4 Hz), 6.31 (1H, d, J=13.6 Hz), 2.76 (2H, m), 2.36 (2H, m), 2.07 (2H, m) ppm. MS: 251.1 (M+H$^+$).

Synthesis of 4-[7-(6-cyano-5-trifluoromethyl-3-pyridyl)-8-oxo-6-thio-5,7-diazaspiro[3,4]-5-octyl]-2-fluoro-N-trideuteromethyl-benzamide (compound 14)

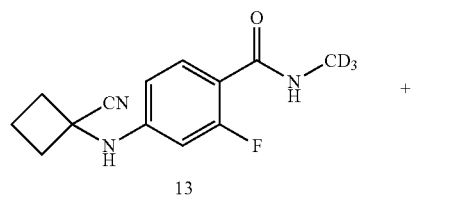

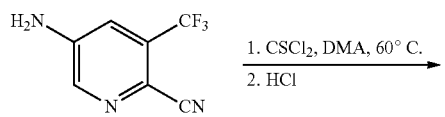

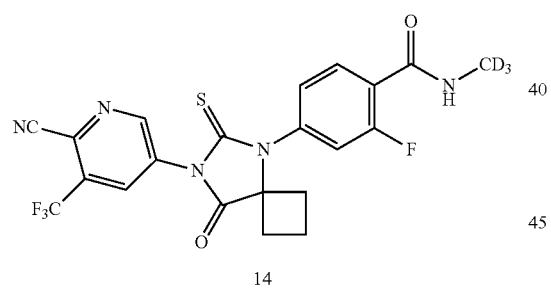

To the mixture of compound 13 (68 mg, 0.26 mmol) and compound 5 (50 mg, 0.26 mmol) in DMA (10 ml), thiophosgene (32 mg, 0.26 mmol) was added in dropwise. The mixture was heated to 60° C. for 16 h, and then methanol (10 mL), water (10 mL) and concentrated hydrochloric acid (2 mL) were added in and the mixture was heated at reflux for 1 h. The resulting mixture was extracted with ethyl acetate, washed with brine, dried over sodium sulfate, concentrated and purified by column chromatography (PE:EA/1:1) to give a brown solid as crude product, which was purified by preparative chromatography to give compound 14 as a white solid (52.3 mg, 43.6% yield). $^1$H NMR (CD$_3$OD, 400 MHz): δ (ppm) 9.17 (1H, d, J=2.0 Hz), 8.65 (1H, d, J=2.0 Hz), 7.95 (1H, m), 7.41 (2H, m), 2.73 (2H, m), 2.60 (2H, m), 2.16 (1H, m), 1.67 (1H, m), MS: 481.2 (M+H$^+$).

Example 3

4-[7-(6-cyano-5-trifluoromethyl-3-pyridyl)-8-oxo-6-thio-5,7-diazaspiro [3,4]-5-octyl]-3,5-bideuterium-2-fluoro-N-methyl-benzamide (Compound 17)

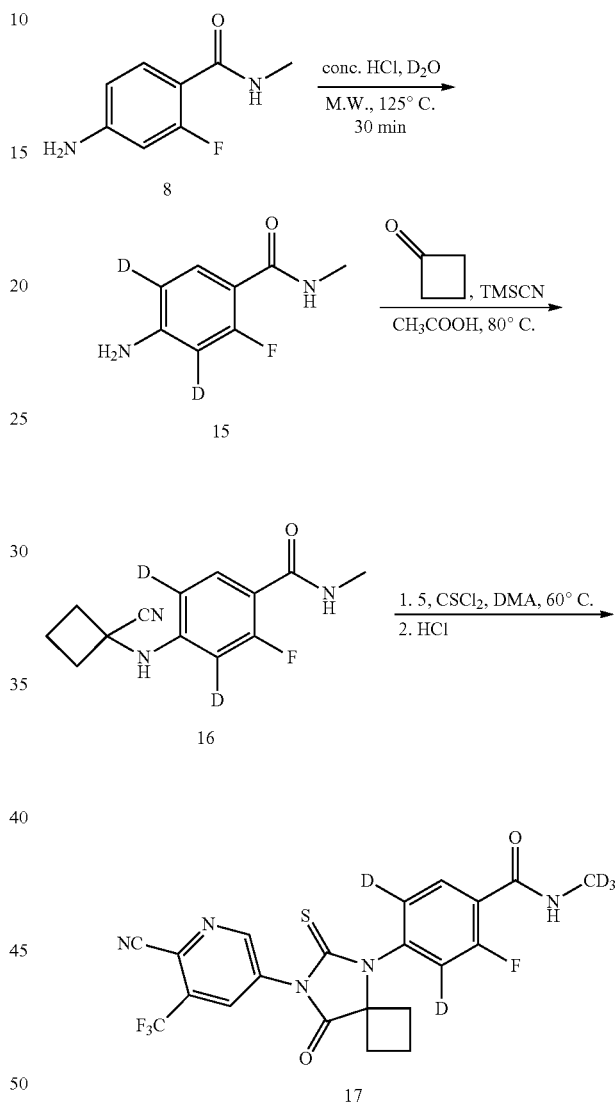

Synthesis of 3,5-di-deuterium-4-amino-2-fluoro-N-methyl-benzamide (Intermediate 15)

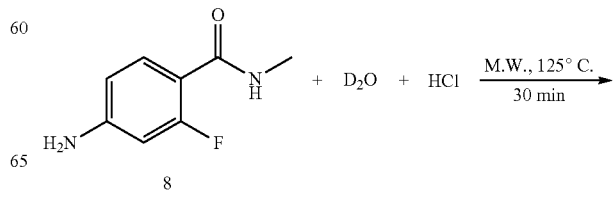

-continued

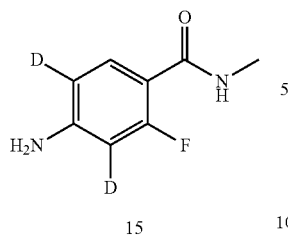

15

To a suspension of compound 8 (1 g, 6.0 mmol) in deuterium oxide (10 ml), concentrated hydrochloric acid (0.5 ml, 6.0 mmol) was added in. The obtained mixture was heated by microwave at 125° C. for 30 min, 75 W. The reaction solution was adjusted to basic by 1M aqueous NaOH, and white solid were precipitated. The resulting mixture was filtered, washed with water (20 ml×3), dried to give a white solid compound 15 (0.8 g, 79.0% yield). 1H NMR (CDCl$_3$, 400 MHz): δ 7.92 (1H, d, J=8.8 Hz), 6.62 (1H, s), 4.10 (2H, s), 2.99 (3H, s) ppm.

Synthesis of 4-(1-cyano-cyclobutylamino)-3, 5-bideuterium-2-fluoro-N-methyl-benzamide (Intermediate 16)

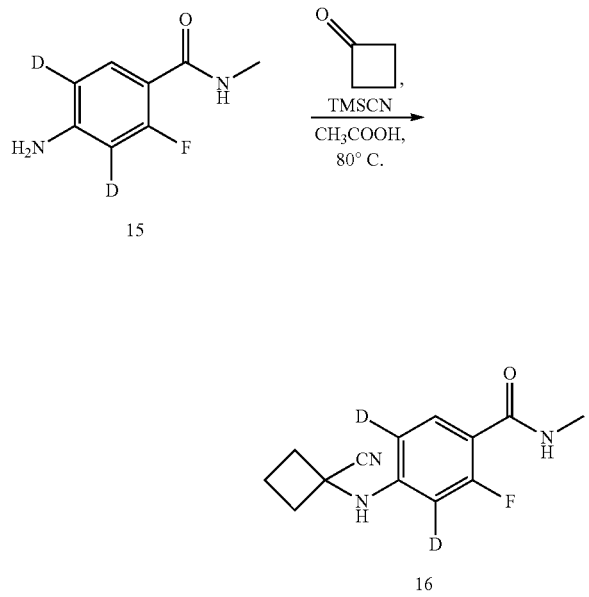

TMSCN (1.77 g, 17.54 mmol), cyclobutanone (0.89 mL, 11.88 mmol), compound 15 (1 g, 5.95 mmol) were dissolved in acetic acid (10 mL). The resulting mixture was stirred at 80° C. for 16 h, and it was cooled to room temperature. Water (10 mL) was added, and the resulting mixture was extracted with ethyl acetate, washed with brine, dried over sodium sulfate, and concentrated. The resulting solid was washed with petroleum ether (10 mL) and was filtered off to give compound 16 as a brown solid (1.31 g, 90% yield). $^1$H NMR (DMSO, 400 MHz): δ 7.79 (1H, s), 7.56 (1H, d, J=8.8 Hz), 7.36 (1H, s) 2.76 (2H, m), 2.36 (2H, m), 2.07 (2H, m) ppm. MS: 250.1 (M+H$^+$)

Synthesis of 4-[7-(6-cyano-5-trifluoromethyl-3-pyridyl)-8-oxo-6-thio-5,7 diazaspiro [3,4]-5-octyl]-3,5-bideuterium-2-fluoro-N-methyl-benzamide (compound 17)

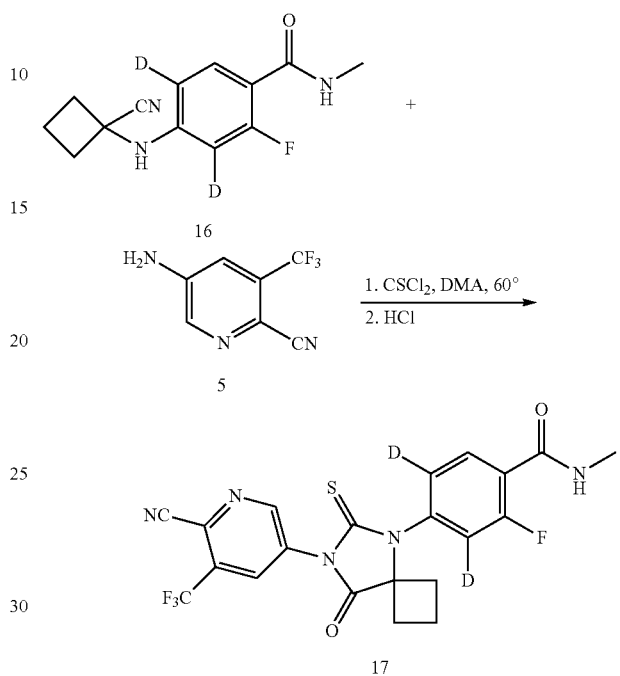

To a mixture of compound 16 (68 mg, 0.26 mmol) and compound 5 (50 mg, 0.26 mmol) in DMA (10 ml), thiophosgene (32 mg, 0.26 mmol) was added in dropwise. The mixture was heated to 60° C. for 16 h. Methanol (10 mL), water (10 mL) and concentrated hydrochloric acid (2 mL) were added in, and the resulting mixture was heated at reflux for 1 h. The mixture was extracted with ethyl acetate, washed with brine, dried over sodium sulfate, and concentrated. A brown solid was obtained by column chromatography (PE:EA/1:1), which was further purified by preparative chromatography to give compound 17 as a white solid (38.4 mg, yield 32%). $^1$H NMR (CD$_3$OD, 400 MHz): δ 9.17 (1H, d, J=2.0 Hz), 8.65 (1H, d, J=2.0 Hz), 7.96 (1H, d, J=8.0 Hz), 2.98 (3H, s), 2.73 (2H, m), 2.60 (2H, m), 2.16 (1H, m), 1.67 (1H, m) ppm. MS: 480.1 (M+H$^+$).

Example 4

Synthesis of 4-[7-(6-cyano-5-trifluoromethyl-3-pyridyl)-8-oxo-6-thio-5,7-diazaspiro[3,4]-5-octyl]-3,5-bideuterium-2-fluoro-N-trideuteromethyl-benzamide (compound 20)

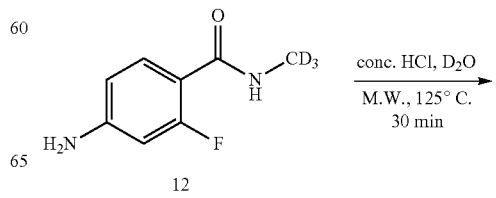

Synthesis of 3, 5-bideuterium-4-amino-2-fluoro-N-trideuteromethyl-benzamide (Intermediate 18)

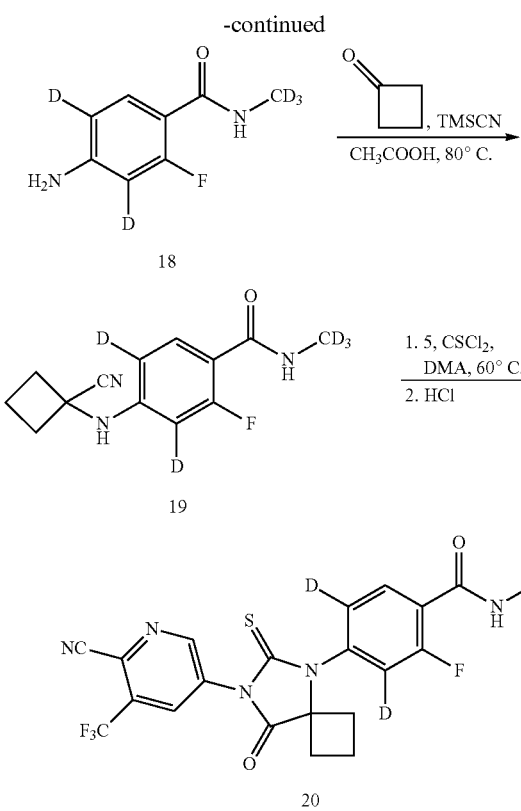

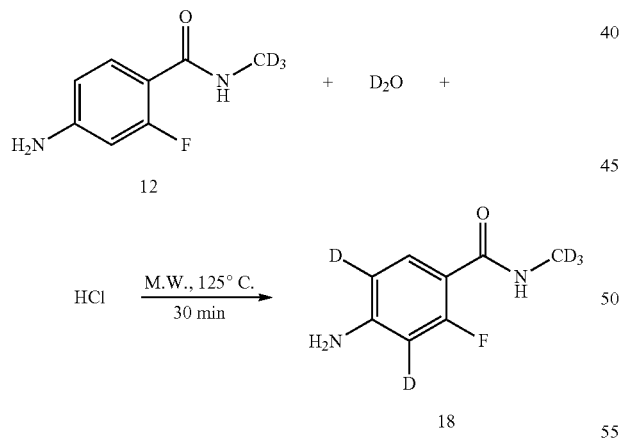

To a suspension of compound 12 (1 g, 6.0 mmol) in deuterium oxide (10 mL), concentrated hydrochloric acid (0.5 ml, 6.0 mmol) was added in. The mixture was heated by microwave at 125° C. for 30 min, 75 W. The reaction solution was adjusted to basic by 1M aqueous NaOH and white solid was precipitated. The resulting mixture was filtered off, washed with water (20 ml×3), dried to give a white solid compound 18 (0.8 g, 79.0% yield). $^1$H NMR (CDCl$_3$, 400 MHz): δ 7.92 (1H, d, J=8.8 Hz), 6.62 (1H, s), 4.10 (2H, s) ppm.

Synthesis of 4-((1-cyanocyclobutyl) amino)-3, 5-bideuterium-2-fluoro-N-trideuteromethylbenzamide (Intermediate 19)

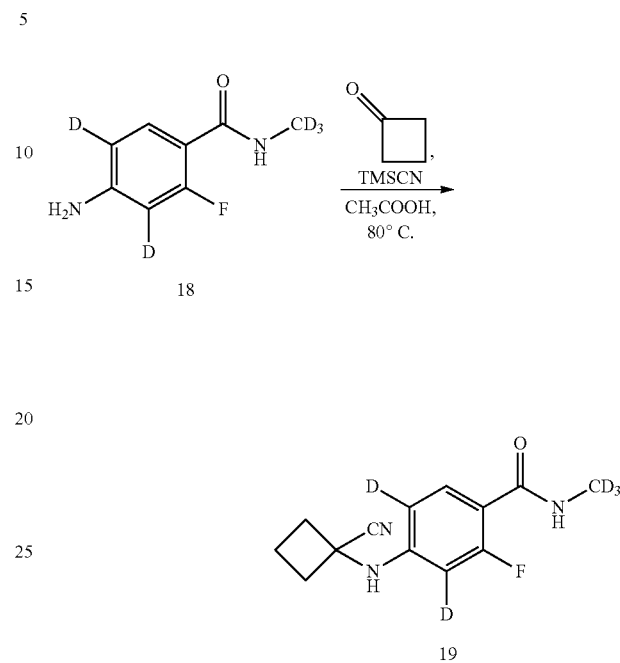

TMSCN (1.77 g, 17.54 mmol), cyclobutanone (0.89 ml, 11.88 mmol), compound 18 (1 g, 5.95 mmol) was dissolved in acetic acid (10 ml), and the mixture was stirred at 80° C. for 16 h. Then it was cooled to room temperature followed by the addition of water (10 ml). The mixture was extracted with ethyl acetate, washed with brine, dried (Na$_2$SO$_4$), concentrated. The resulting residue was washed with petroleum ether, filtrated off and dried to give brown solid 19 (1.31 g, 90% yield). $^1$H NMR (DMSO, 400 MHz): δ 7.79 (1H, s), 7.561 (H, d, J=8.8 Hz), 7.36 (1H, s), 2.76 (2H, m), 2.36 (2H, m), 2.07 (2H, m) ppm. MS: 253.1 (M+H$^+$).

Synthesis of 4-(7-(6-cyano-5-(trifluoromethyl) pyridin-3-yl)-8-oxo-6-thioxo-5, 7-diazaspiro [3.4]octan-5-yl)-3,5-bideuterium-2-fluoro-N-methylbenzamide (compound 20)

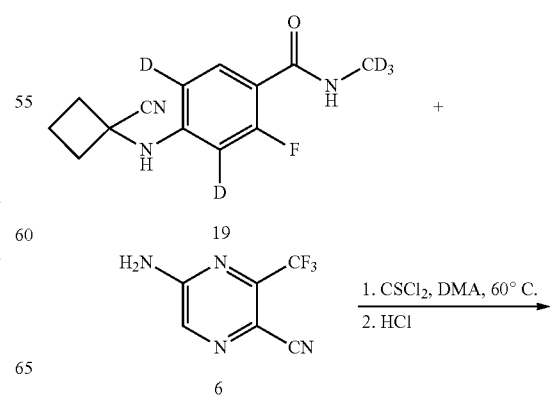

27

-continued

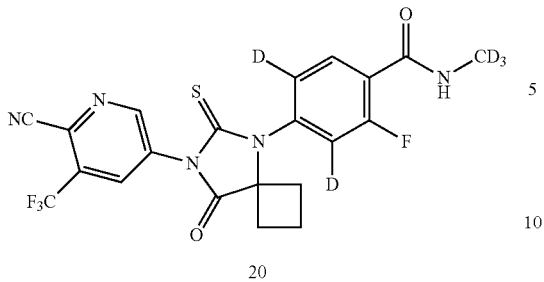

20

28

-continued

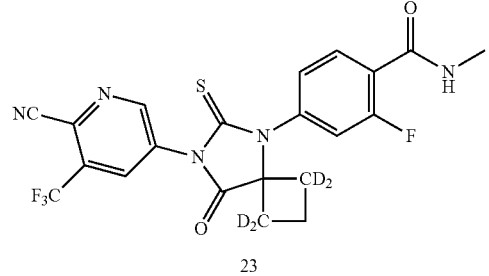

23

Compound 19 (68 mg, 0.26 mmol) and compound 5 (50 mg, 0.26 mmol) were dissolved in DMA (10 ml), followed by the addition of thiophosgene (32 mg, 0.26 mmol). The mixture was stirred at 60° C. for 16 h, and methanol (10 ml), water (10 ml) and concentrated HCl (2 ml) was added in. The resulting mixture was heated at refluxing for 1 h. The resulting mixture was extracted with ethyl acetate, washed with brine, dried over sodium sulfate, and concentrated. The residue was purified by column chromatography (PE:EA/1: 1) to give a brown solid which was further purified by preparative chromatography to give compound 20 as a white solid (48 mg, 40% yield). $^1$H NMR (CD$_3$OD, 400 MHz): δ 9.17 (1H, d, J=2.0 Hz), 8.65 (1, d, J=2.0 Hz), 7.95 (1H, d, J=8.0 Hz), 2.73 (2H, m), 2.60 (2H, m), 2.16 (1H, m), 1.67 (1H, m) ppm. MS: 483.3 (M+H$^+$).

Example 5

Synthesis of 4-[1,1,3,3-tetradeuterated-(7-(6-cyano-5-(trifluoromethyl)pyridin-3-yl)-8-oxo-6-thioxo-5,7-diazaspiro[3.4]octan-5-yl)]-2-fluoro-N-methylbenzamide (compound 23)

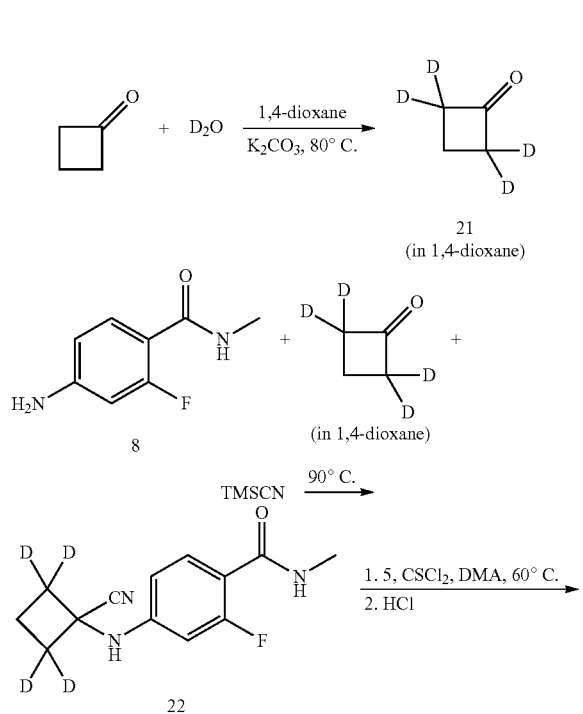

Synthesis of 2, 2, 4, 4-tetradeuteratedcyclobutan-1-one (intermediate 21)

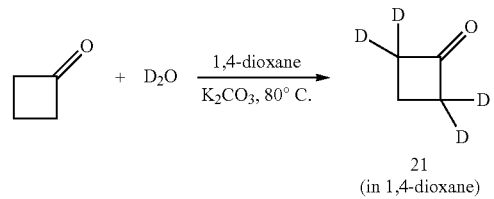

Cyclobutanone was dissolved in the mixture of 1,4-dioxane and D$_2$O (30 ml:10 ml), potassium carbonate (10 g, 72.5 mmole) was added in. The reaction was warmed to 75° C. for 24 h. Then it was cooled to room temperature, and the organic layer was isolated for the use of next step directly.

Synthesis of 4-[(1-cyano-2,2,4,4-tetradeuterated-cyclobutyl)amino]-2-fluoro-N-methylbenzamide. (intermediate 22)

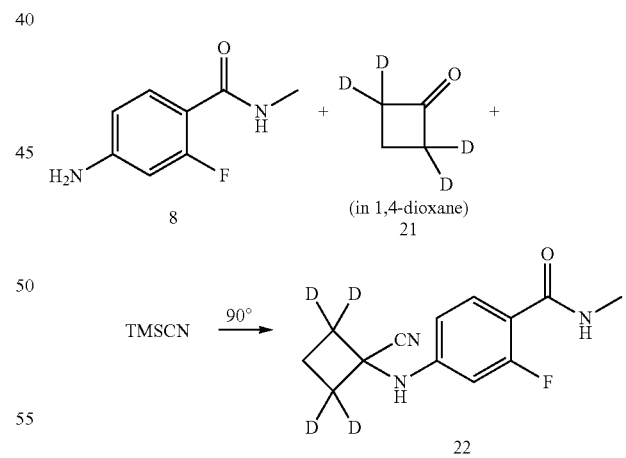

TMSCN (0.5 ml), compound 21, and compound 8 (70 g, 0.42 mmol) were dissolved in 1, 4-dioxane (5 mL). The mixture was stirred at 80° C. overnight, and then it was concentrated. The residue was purified by flash column chromatography to give white solid 22 (54 mg, 52% yield). $^1$H NMR (CDCl$_3$, 400 MHz): δ 8.00 (1H, m), 6.62 (1H, br), 6.49 (1H, d, J=8.4 Hz), 6.30 (1H, d, J=14 Hz), 4.51 (1H, br), 3.01 (3H, s), 2.23 (1H, d, J=12 Hz), 2.16 (1H, d, J=12 Hz) ppm.

Synthesis of 4-[1,1,3,3-tetradeuterated-(7-(6-cyano-5-(trifluoromethyl)pyridin-3-yl)-8-oxo-6-thioxo-5,7-diazaspiro[3.4]octan-5-yl)]-2-fluoro-N-methylbenzamide (compound 23)

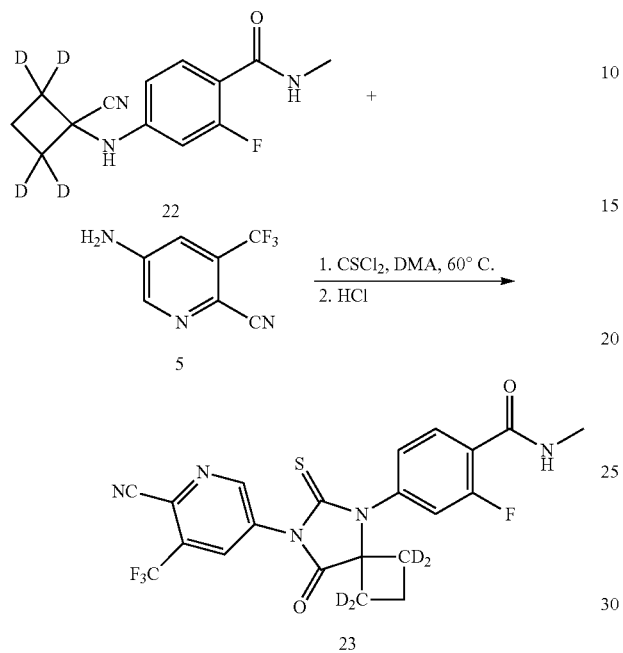

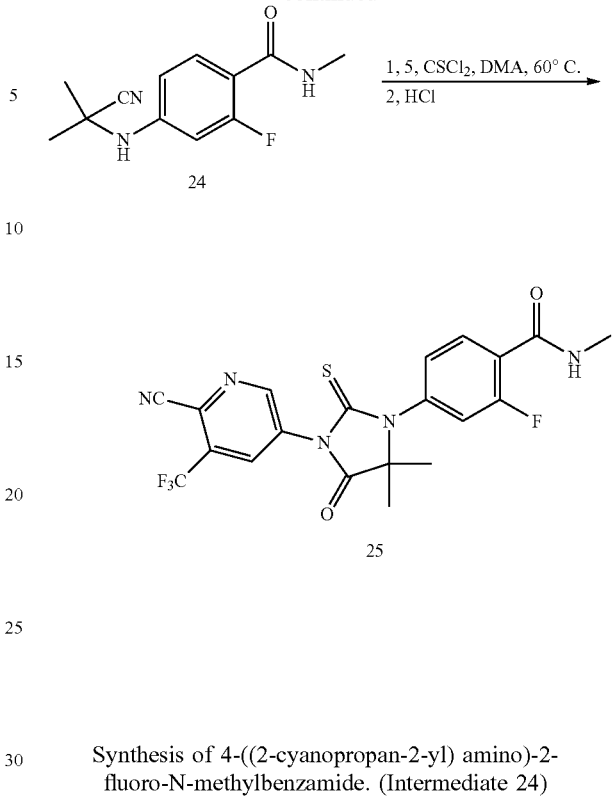

Compound 22 (54 mg, 0.21 mmol) and compound 5 (37 mg, 0.21 mmol) were dissolved in DMA (10 ml) followed by the addition of thiophosgene (25.6 mg, 0.21 mmol). The mixture was stirred at 60° C. for 16 h, and methanol (10 ml), water (10 ml) and concentrated HCl (2 ml) were added to the reaction mixture. The resulting mixture was heated at refluxing for 1 h. The resulting mixture was extracted with ethyl acetate, washed with brine, dried over sodium sulfate, and concentrated. The residue was purified by column chromatography (PE:EA/1:1) to give a brown solid, which was further purified by preparative chromatography to give compound 20 as a white solid (23 mg, 39.6% yield). $^1$H NMR (CD$_3$OD, 400 MHz): δ 9.17 (1H, d, J=1.6 Hz), 8.65 (1H, d, J=1.6 Hz), 7.95 (1H, m), 7.41 (2H, m), 2.98 (3H, s), 2.13 (1H, m), 1.64 (1H, m) ppm. MS: 482.2 (M+H$^+$).

Example 6

Synthesis of 4-{7-[6-cyano-5-(trifluoromethyl) pyridin-3-yl]-5,5-dimethyl-4-oxo-2-thioxoimidazolidin-1-yl}-2-fluoro-N-methylbenzamide (compound 25)

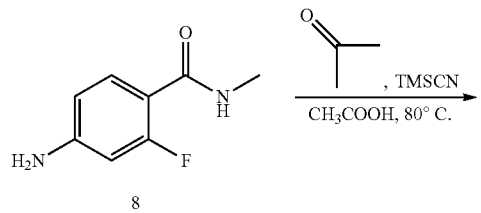

Synthesis of 4-((2-cyanopropan-2-yl) amino)-2-fluoro-N-methylbenzamide. (Intermediate 24)

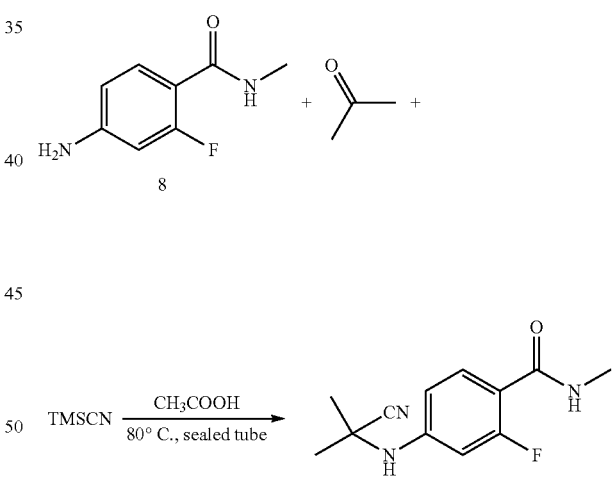

TMSCN (5 g, 50.4 mmol) and compound 8 (2 g, 11.89 mmol) were dissolved in a solution of acetic acid (10 mL) and acetone (10 mL). The resulting mixture was stirred at 80° C. overnight (16 h), and then it was cooled to room temperature. Water was added in (20 mL), and the resulting mixture was extracted with ethyl acetate, washed with brine, dried over sodium sulfate, and concentrated. The resulting solid was washed with petroleum ether (10 mL) and dried to give compound 24 as a white solid (2.6 g, 91.5% yield). $^1$H NMR (CDCl$_3$, 400 MHz): δ 7.97 (1H, m), 6.65 (1H, s), 6.62 (1H, d, J=5.2 Hz), 6.59 (1H, d, J=14.8 Hz), 4.40 (1H, s), 3.01 (3H, d, J=4 Hz), 1.76 (6H, s) ppm.

Synthesis of 4-(7-(6-cyano-5-(trifluoromethyl)pyridin-3-yl)-5,5-dimethyl-4-oxo-2-thioxoimidazolidin-1-yl)-2-fluoro-N-methylbenzamide. (compound 25)

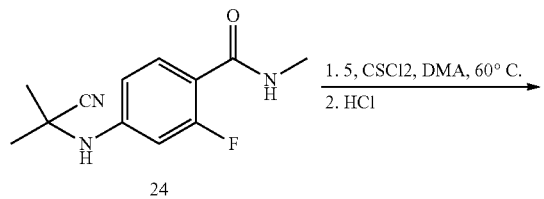

24

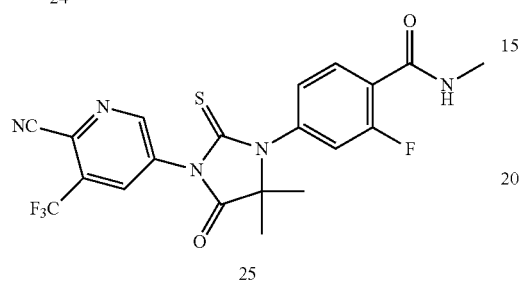

25

Compound 24 (68 mg, 0.26 mmol) and compound 5 (50 mg, 0.26 mmol) were dissolved in DMA (10 ml), followed by the addition of thiophosgene (25.6 mg, 0.21 mmol). The mixture was stirred at 60° C. for 16 h, and methanol (10 ml), water (10 ml) and concentrated HCl (2 ml) were added in. The resulting mixture was heated at refluxing for 1 h. The resulting mixture was extracted with ethyl acetate, washed with brine, dried over sodium sulfate, and concentrated. The residue was purified by column chromatography (PE:EA/1:1) to give a brown solid, which was further purified by preparative chromatography to give compound 25 as a white solid (48 mg, 40% yield). $^1$H NMR (CD$_3$OD, 400 MHz): δ 9.19 (1H, d, J=1.6 Hz), 8.70 (1H, d, J=1.6 Hz), 7.91 (1H, m), 7.40 (2H, m), 2.97 (3H, s), 1.63 (6H, s) ppm. MS: 465.1 (M+H$^+$).

Example 7

Synthesis of 4-(7-(6-cyano-5-(trifluoromethyl)pyridin-3-yl)-5,5-dimethyl-4-oxo-2-thioxoimidazolidin-1-yl)-2-fluoro-N-trideuteratedmethylbenzamide. (compound 27)

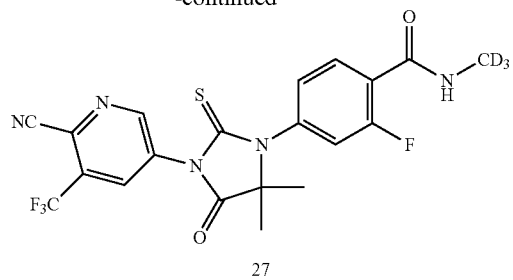

27

Synthesis of 4-((2-cyanopropan-2-yl)amino)-2-fluoro-N-trideuteratedmethyl-benzamide (intermediate 26)

TMSCN (4 g, 40.3 mmol) and compound 12 (1.5 g, 8.8 mmol) were dissolved in a solution of acetic acid (10 mL) and acetone (10 mL). The resulting mixture was stirred at 80° C. overnight (16 h), and then it was cooled to room temperature. Water was added in (20 mL), and the resulting mixture was extracted with ethyl acetate, washed with brine, dried over sodium sulfate, and concentrated. The resulting solid was washed with petroleum ether (10 mL) and dried to give compound 26 as a white solid (2 g, 93.4% yield).

Synthesis of 4-(7-(6-cyano-5-(trifluoromethyl)pyridin-3-yl)-5,5-dimethyl-4-oxo-2-thioxoimidazolidin-1-yl)-2-fluoro-N-trideuteratedmethylbenzamide. (compound 27)

33
-continued

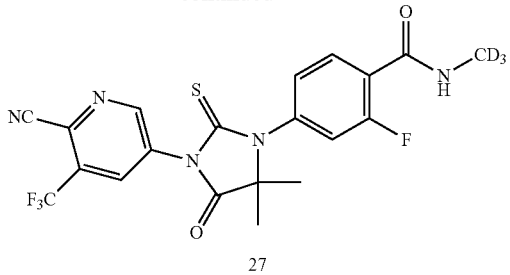

Compound 26 (68 mg, 0.26 mmol) and compound 5 (50 mg, 0.26 mmol) were dissolved in DMA (10 ml) followed by the addition of thiophosgene (32 mg, 0.26 mmol). The mixture was stirred at 60° C. for 16 h, and methanol (10 ml), water (10 ml) and concentrated HCl (2 ml) were added to the reaction mixture the resulting mixture was heated at reflux for 1 h. The resulting mixture was extracted with ethyl acetate, washed with brine, dried over sodium sulfate, and concentrated. The residue was purified by column chromatography (PE:EA/1:1) to give a brown solid, which was further purified by preparative chromatography to give compound 27 as a white solid (48 mg, 40% yield). $^1$H NMR (CD$_3$OD, 400 MHz): δ 9.19 (1H, d, J=1.6 Hz), 8.70 (1H, d=1.6 Hz) 7.91 (1H, m), 7.39 (2H, m), 1.63 (6H, s) ppm. MS: 469.2 (M+H$^+$).

Example 8

Synthesis of 4-(7-(6-cyano-5-(trifluoromethyl) pyridin-3-yl)-5, 5-bitrideuteratedmethyl-4-oxo-2-thioxoimidazolidin-1-yl)-2-fluoro-N-methylbenzamide. (compound 29)

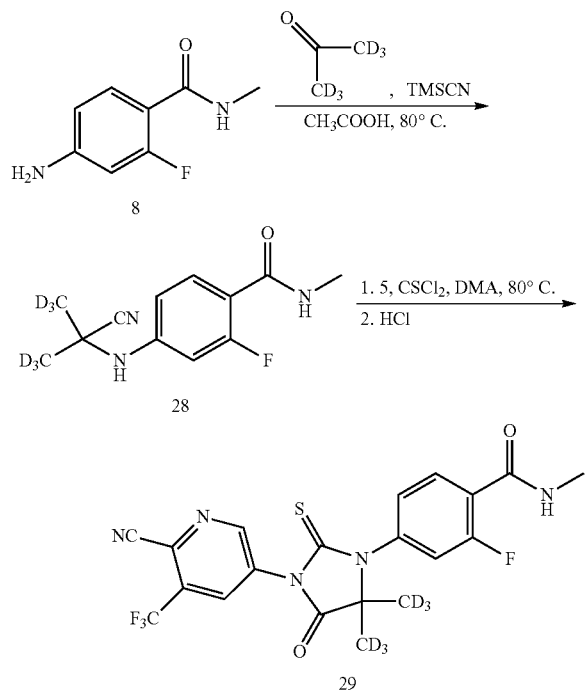

34

Synthesis of 4-[(2-cyanopropan-2,2-bitrideuterated-methyl)amino]-2-fluoro-N-methylbenzamide (intermediate 28)

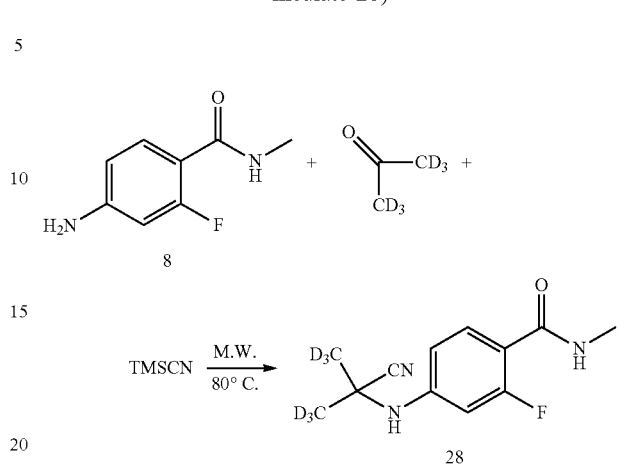

TMSCN (2.1 g, 21.2 mmol) and compound 8 (0.7 g, 4.2 mmol) were dissolved in a solution of deuterated propan-2-one (1.5 g, 23.4 mmol) in microwave reaction tube. The resulting mixture was stirred in a microwave reaction tube at 80° C. 3 h at the power of 50 w, and then it was cooled to room temperature. Water was added (20 mL), and the resulting mixture was extracted with ethyl acetate, washed with brine, dried over sodium sulfate, and concentrated. The resulting solid was washed with petroleum ether (10 mL) and dried to give compound 28 as a white solid (870 mg, 86.6% yield).

Synthesis of 4-(7-(6-cyano-5-(trifluoromethyl) pyridin-3-yl)-5, 5-bitrideuteratedmethyl-4-oxo-2-thioxoimidazolidin-1-yl)-2-fluoro-N-methylbenzamide. (compound 29)

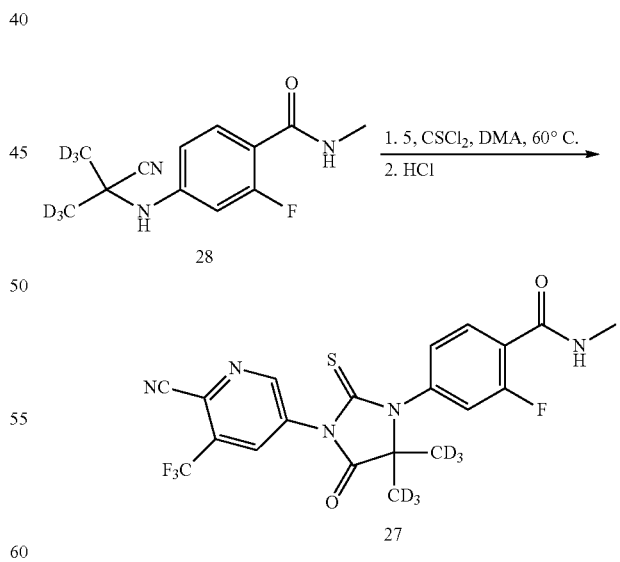

Compound 28 (68 mg, 0.26 mmol) and compound 5 (50 mg, 0.26 mmol) were dissolved in DMA (10 ml) followed by the addition of thiophosgene (32 mg, 0.26 mmol). The mixture was stirred at 60° C. for 16 h, and methanol (10 ml), water (10 ml) and concentrated HCl (2 ml) were added to the reaction mixture the resulting mixture was heated at reflux for 1 h. The resulting mixture was extracted with ethyl acetate, washed with brine, dried over sodium sulfate, and concentrated. The residue was purified by column chromatography (PE:EA/1:1) to give a brown solid which was further purified by preparative chromatography to give compound 29 as a white solid (48 mg, 40% yield). $^1$H NMR (CD$_3$OD, 400 MHz): δ 9.19 (1H, d, J=1.2 Hz), 8.70 (1H, d=1.2 Hz), 7.91 (1H, m), 7.39 (2H, m), 2.97 (3H, s) ppm. MS: 472.2 (M+H$^+$).

Example 9 synthesis of 4-(7-(6-cyano-5-(trifluoromethyl)pyridin-3-yl)-5,5-bitrideuteratedmethyl-4-oxo-2-thioxoimidazolidin-1-yl)-2-fluoro-N-trideuteratedmethylbenzamide (compound 31)

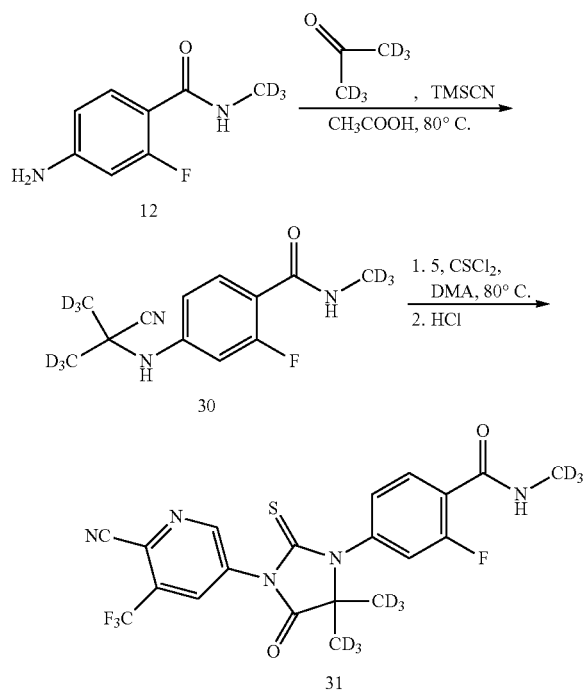

Synthesis of 4-((2-cyanopropan-2,2-bitrideuteratedmethyl)amino)-2-fluoro-N-trideuteratedmethylbenzamide (intermediate 30)

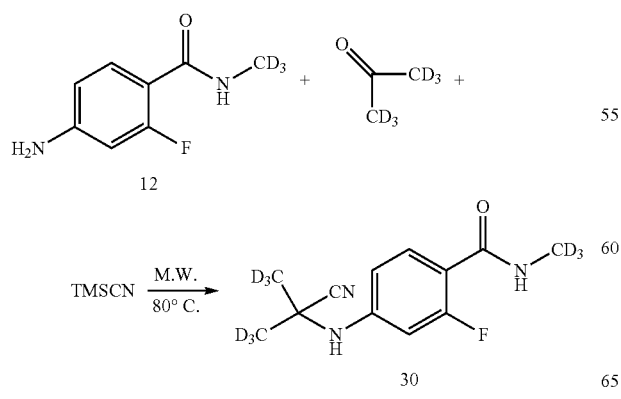

TMSCN (2.1 g, 21.2 mmol) and compound 12 (0.7 g, 4.2 mmol) were dissolved in a solution of deuterated propan-2-one (1.5 g, 23.4 mmol) in microwave reaction tube. The resulting mixture was stirred in a microwave reaction tube at 80° C. 3 h at the power of 50 w, and then it was cooled to room temperature. water was added in (20 mL), and the resulting mixture was extracted with ethyl acetate, washed with brine, dried over sodium sulfate, and concentrated. The resulting solid was washed with petroleum ether (10 mL) and dried to give compound 30 as a white solid (870 mg, 86.6% yield).

synthesis of 4-(7-(6-cyano-5-(trifluoromethyl)pyridin-3-yl)-5,5-bitrideuteratedmethyl-4-oxo-2-thioxoimidazolidin-1-yl)-2-fluoro-N-trideuteratedmethylbenzamide (compound 31)

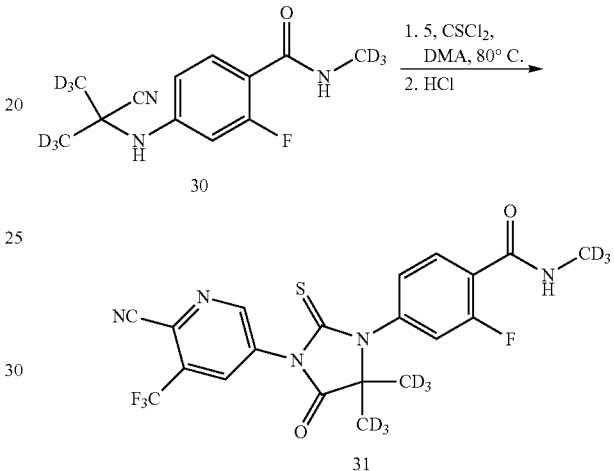

Compound 30 (68 mg, 0.26 mmol) and compound 5 (50 mg, 0.26 mmol) were dissolved in DMA (10 ml), followed by the addition of thiophosgene (32 mg, 0.26 mmol) it was stirred at 60° C. for 16 h, and methanol (10 ml), water (10 ml) and concentrated HCl (2 ml) was added in. The resulting mixture was heated at reflux for 1 h. The resulting mixture was extracted with ethyl acetate, washed with brine, dried over sodium sulfate, and concentrated. The residue was purified by column chromatography (PE:EA/1:1) to give a brown solid which was further purified by preparative chromatography to give compound 31 as a white solid (48 mg, 40% yield). $^1$H NMR (CD$_3$OD, 400 MHz): δ 9.19 (1H, d, J=1.6 Hz), 8.70 (1H, d, J=1.6 Hz), 7.91 (1H, m), 7.39 (2H, m) ppm. MS: 475.1 (M+H$^+$).

Compound 33, 35, 36, 37, 38, 40, 41, 42, 43 were synthesized according to the way of compound 14.

compound 33

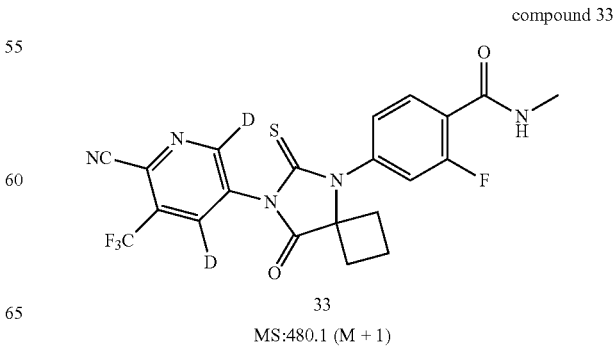

MS:480.1 (M + 1)

-continued

Compound 35

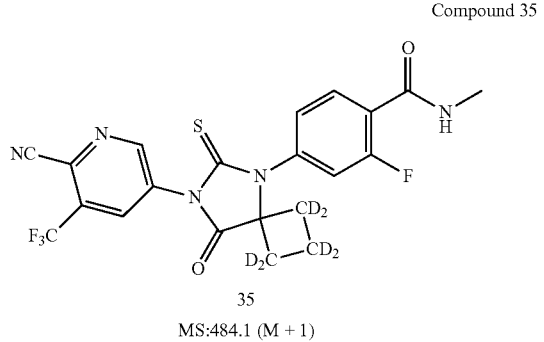

35
MS:484.1 (M+1)

compound36

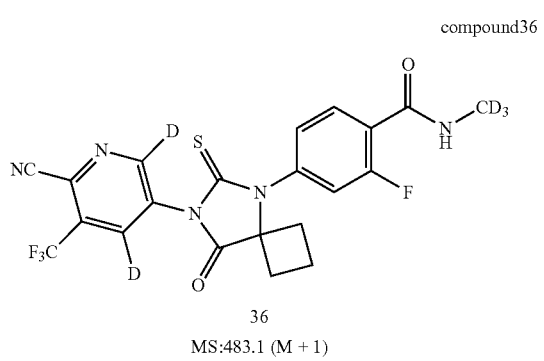

36
MS:483.1 (M+1)

compound37

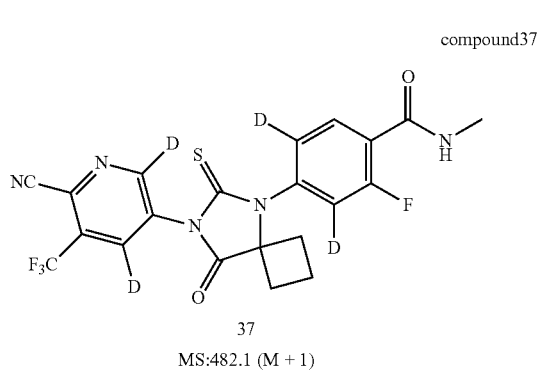

37
MS:482.1 (M+1)

compound38

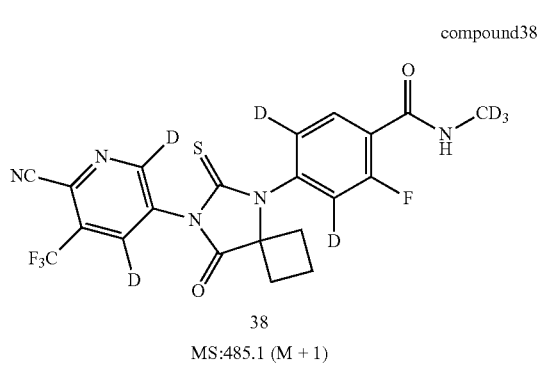

38
MS:485.1 (M+1)

-continued compound40

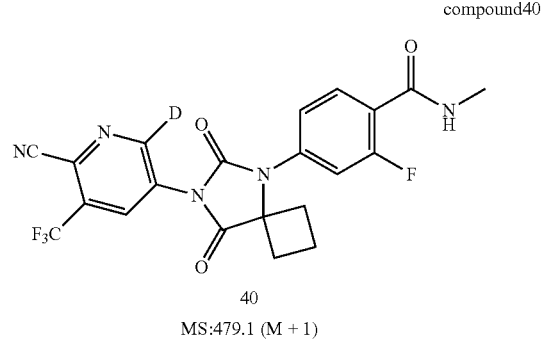

40
MS:479.1 (M+1)

compound41

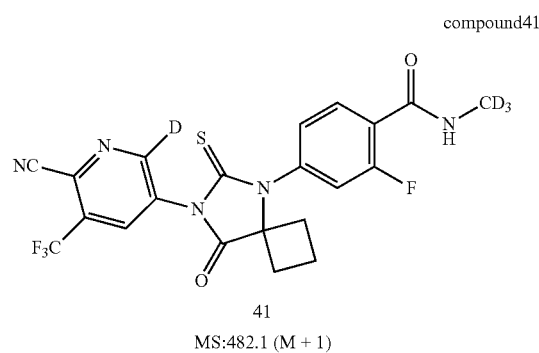

41
MS:482.1 (M+1)

compound42

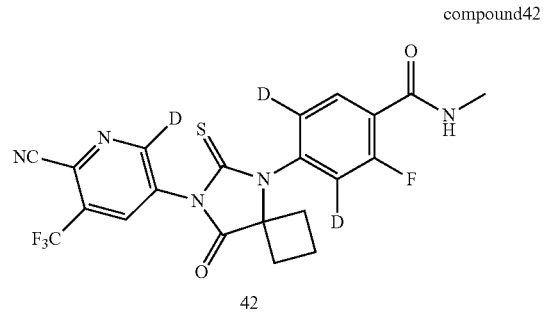

42
MS:481.1 (M+1)

compound43

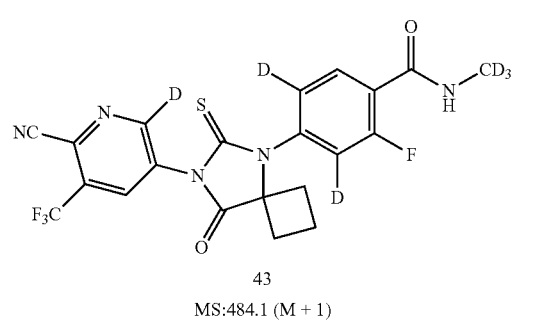

43
MS:484.1 (M+1)

Test Case 1: Evaluation of Pharmacokinetics in Mice 10 mg/kg compound 10, 14, 17, 20 were intragastrically administered to Healthy Kunming mice (KM mice), male, weighing 18-20 g. Compounds were dissolved in DMSO:PEG400:$H_2O$ 1:5:14. The volume of administration was 10 mL/kg. Before testing, the mice fasted for 12 h and drunk water ad libitum. Then, the mice were fed together at 2 h after administration. 0.3 mL of blood were took from 3 mice through retrobulbar venous plexus at 0.5, 1.0, 2.0, 4.0, 6.0 and 24 h after administration, placed in heparinized tubes, and centrifuged for 5 min at 11000 rpm. The plasma was separated and frozen in a refrigerator at −20° C. 100 uL of serum was transferred with a pipettor into a clean plastic centrifuge tube marked with compound's name and time point, and diluted with acetonitrile (CH3CN) and centrifuged. The concentration of drug was analyzed by LC-MS. Serum was stored at −80° C. before analysis.

The pharmacokinetic parameters of deuterated compound (compound 14, 17, and 20) and undeuterated compound (compound 10) were show in following table. The experimental results showed that, compared with corresponding undeuterated compound 10, Cmax and AUC of the deuterated compound 14 or 20 of the present invention were significantly increased, in which AUC was increased by at least 20%.

TABLE 1 the Pharmacokinetics in mice

| compound | $T_{max}$ (h) | $C_{max}$ (μg/ml) | $AUC_{0-t}$ (μg/L*h) |
|---|---|---|---|
| 10 (ARN509) | 6 | 3.32 | 61.56 |
| 14 | 4 | 4.48 | 87.84 |
| 17 | 6 | 3.48 | 63.79 |
| 20 | 4 | 3.94 | 80.62 |

Test Case 2: Evaluation of Pharmacokinetics in Rats.

10 mg/kg compound 10, and 14 were intragastrically administered to SD rats male, weighing 18-20 g. Compounds were dissolved in DMSO:PEG400:$H_2O$ 1:5:14. The volume of administration was 10 mL/kg. Conventional methods were used for the results evaluation. The results were shown in the following table:

TABLE 2 the pharmacokinetic parameters of rats after given 10 mg/kg of different compounds (n = 4)

| Treat | | Tmax (h) | Cmax (ng/ml) | AUClast (h*ng/ml) | AUCINF_obs (h*ng/ml) | MRT (h) | T1/2 (h) |
|---|---|---|---|---|---|---|---|
| 10(ARN509) | Mean | 3.500 | 946.0 | 13104 | 14752 | 10.692 | 7.379 |
| | SD | 0.577 | 42.6 | 1659 | 1997 | 0.490 | 0.240 |
| | CV% | 16.5 | 4.5 | 12.7 | 13.5 | 4.6 | 3.3 |
| 14 | Mean | 3.500 | 1696.8 | 24063 | 28729 | 12.993 | 8.933 |
| | SD | 0.577 | 291.7 | 2275 | 752 | 3.175 | 2.201 |
| | CV% | 16.5 | 17.2 | 9.5 | 2.6 | 24.4 | 24.6 |

The data in Table 2 show that: compared with non-deutertated compound 10, deuterated compounds 14 showed longer half-life, much bigger Cmax and AUC, which is about 2 fold of compound 10.

Test Cases 3: In Vitro Tests

The ability of compounds to inhibit the growth of prostate cancer cells was tested:

First, the human prostate cancer LNCaP (purchased from ATCC, USA) was transferred to a RPM11640 culture medium containing 10% charcoal-stripped fetal bovine serum (FBS). After cultured for three days, the cells were digested with 0.25% trypsin and counted through trypan blue staining. The cells were plated, with 100 μL cell suspension containing 4000 cells per well. 200 μL medium was added to the wells around the cell plate for avoiding edge effects.

The next day, 6 drug concentrations was prepared (48.6 μM, 19.44 μM, 7.776 μM, 3.11 μM, 1.24 μM, 0.5 μM) before administration, and 100 μL of corresponding compound at corresponding concentration was added into each well of a cell plate. The cell plate was placed in a cell incubator for 30 min, 10 μL of 4 nM R1881 was added into each well and homogeneously mixed. Upon the addition of R1881, the cell plate was placed in a cell incubator and incubated at 37° C., under 5% $CO_2$ for 96 hours. Afterwards, 40 μL of MTT (prepared in PBS, concentration is 2.5 mg/mL) was added into each wells, and incubated at 37° C. for 2 hours. The supernatant was sucked off, and 100 μL of DMSO was added into each well. The plate was shaken by a vibrator for 10 min for dissolving formazan. The plate was read at 570 nm wavelength using a microplate reader in the unit of OD. The inhibition rate of test compounds was calculated with the following equation:

$$IR\ (\%) = (OD_{control} - OD_{sample})/(OD_{control} - OD_{blank}) \times 100\%$$

The inhibition rate curve of test compounds was plotted using the software XLFit (Formula 205), which can calculate the 50% inhibition rate, i.e. $IC_{50}$.

The results are shown in Table 3. The results demonstrate that, compared with compound 10, the compound 14 of the present invention exhibit better inhibition on the growth of prostate cancer cell.

TABLE 3 the inhibition activity on LNCap/AR cell

| The tested compounds | $IC_{50}$ (nM) |
|---|---|
| Compound 10 (ANR509) | 636.9 |
| Compound 14 | 279.9 |

In summary, the compounds of the present invention, with significantly better pharmacokinetic and/or pharmacodynamic properties, is suitable as the androgen receptor antagonist, which could be applied in treatment of male hormone related diseases (such as cancer) drugs.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:

1. An imidazolidinedione compound selected from the group consisting of:

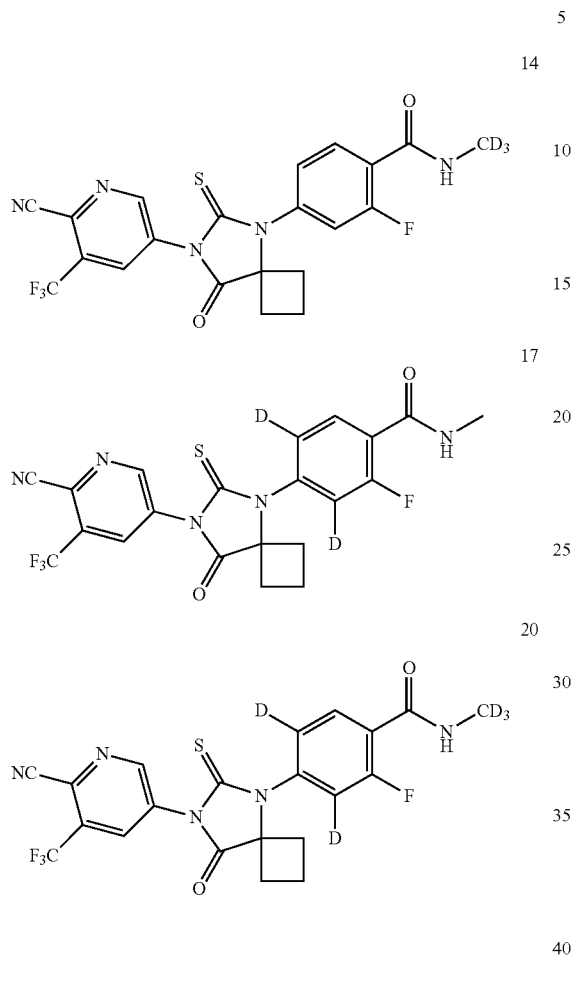

or a crystal form thereof, or a pharmaceutically acceptable salt thereof.

2. The compound of claim 1, wherein the compound is the compound of formula 14, a crystal form thereof or a pharmaceutically acceptable salt thereof.

3. A method for preparing the compound of claim 1, the method comprising the steps of:

(1) under acidic conditions, in the presence of a cyanide, reacting compound 5a with $R_7C(O)R_8$, to form compound 6a,

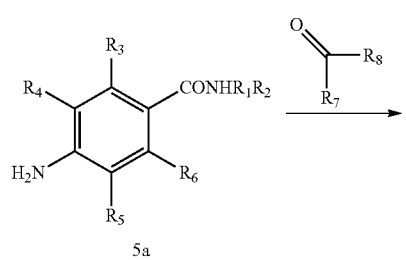

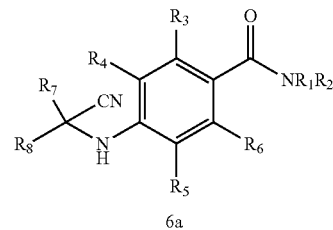

wherein, the cyanide is trimethylsilycyanide, sodium cyanide or potassium cyanide, and (2) in an aprotic solvent, under acidic conditions, reacting compound 2a with compound 6a, to form the compound of formula 14, 17, or 20,

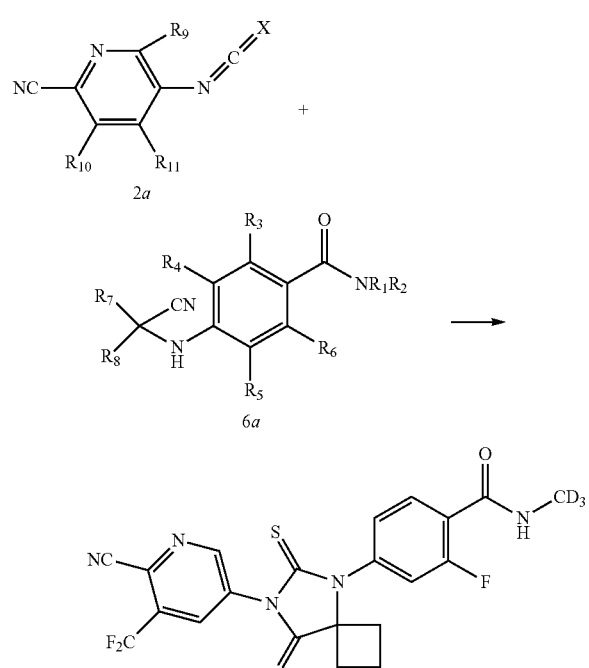

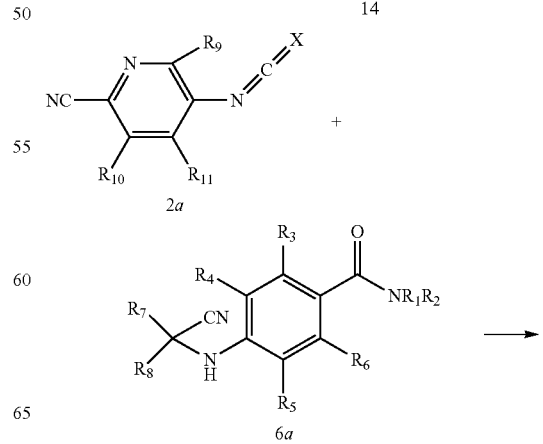

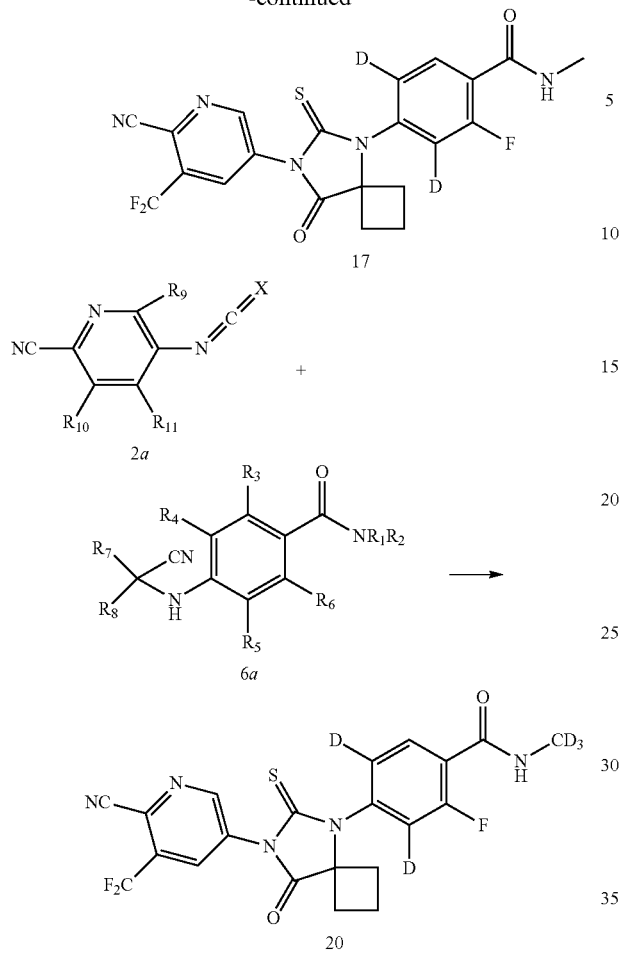

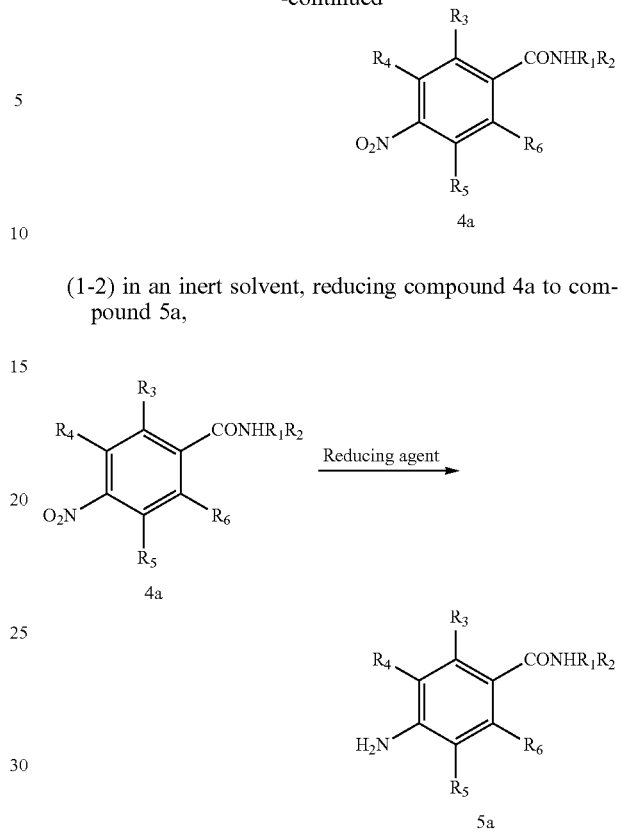

wherein R₁ and R₂ are independently selected from hydrogen, deuterium, $C_1$-$C_4$ alkyl, and one or more deuterium-substituted or perdeuterated $C_1$-$C_4$ alkyl, with the proviso that R₁ and R₂ are not both hydrogen;

$R_3$, $R_4$, $R_5$, $R_6$, $R_9$, and $R_{11}$ are independently hydrogen, deuterium, or halogen;

$R_7$ and $R_8$ are independently $C_1$-$C_4$ alkyl or one or more deuterium-substituted or perdeuterated $C_3$-$C_6$ cycloalkyl;

$R_{10}$ is $C_1$-$C_4$ alkyl or one or more deuterium-substituted or perdeuterated $C_1$-$C_4$ alkyl, or one or more halogen-substituted or perhalogenated $C_1$-$C_4$ alkyl; and X is S or O.

4. The method of claim 3, wherein the method further comprises the following steps prior to step (1):
(1-1) in an inert solvent, reacting compound 3a with $NHR_1R_2$, to form compound 4a,

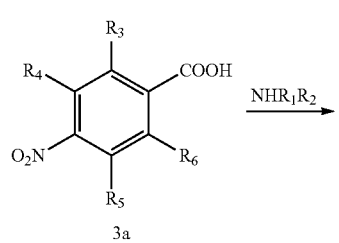

(1-2) in an inert solvent, reducing compound 4a to compound 5a,

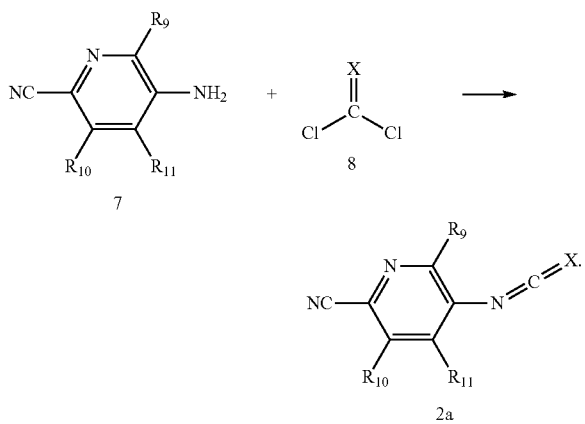

5. The method of claim 3, wherein the method further comprises the following steps prior to step (2):
reacting compound 7 with compound 8 to form compound 2a:

6. A method for treatment of alopecia, hair regeneration, pimples, acne, or prostate cancer, the method comprising administering the compound of claim 1 or a crystal form thereof or a pharmaceutically acceptable salt thereof to a patient in need thereof.

7. A pharmaceutical composition, the composition comprising (1) the compound of claim 1, or a crystal form thereof or a pharmaceutically acceptable salt thereof, and (2) a pharmaceutically acceptable carrier.

* * * * *